United States Patent [19]
Dzau et al.

[11] Patent Number: 5,556,780
[45] Date of Patent: Sep. 17, 1996

[54] CDNAS ENCODING MOUSE AND RAT TYPE-2 ANGIOTENSIN II RECEPTORS AND THEIR EXPRESSION IN HOST CELLS

[75] Inventors: Victor Dzau; Masahi Mukoyama, both of Stanford, Calif.

[73] Assignee: The Board of Trustees for the Leland Stanford Junior University, Stanford, Calif.

[21] Appl. No.: 148,209

[22] Filed: Nov. 5, 1993

Related U.S. Application Data

[63] Continuation-in-part of Ser. No. 100,486, Jul. 30, 1993.

[51] Int. Cl.⁶ .......................... C12N 15/12; C12N 15/63; C12N 5/10; C12N 1/21

[52] U.S. Cl. .................. 435/240.2; 536/23.5; 435/320.1; 435/252.3; 435/254.11; 435/69.1

[58] Field of Search ................ 536/23.5; 435/320.1, 435/240.2, 252.3, 254.11, 69.1

[56] References Cited

PUBLICATIONS

Nakajima et al., (1993) *Biochem. Biophys. Res. Comm.* 197(2): 393–99.
Grady et al. (1991) *J. Clin. Invest.* 88: 921–33.
Whitebread et al. (1991) *Biochem. Biophys. Res. Comm.* 181: 1365–71.
Gearing et al. (1989) *EMBO J.* 8: 3667–76.
Jüppner et al. (1991) *Science* 254: 1024–26.
Mukoyama et al., GenBank database record, accession no. U01908.
Kambayashi et al., GenBank database record, accession no. D16840.
Ichiki et al., GenBank database record, accession no. U00768.

*Primary Examiner*—Stephen G. Walsh
*Assistant Examiner*—David L. Fitzgerald
*Attorney, Agent, or Firm*—Bertram I. Rowland

[57] ABSTRACT

An angiotensin II type 2 receptor ($AT_2$ receptor), structurally related cell receptors, nucleic acids encoding such $AT_2$ receptors, $AT_2$ receptor-related peptides, and methods of using $AT_2$ receptors and $AT_2$ receptor-encoding nucleic acids are provide. $AT_2$ receptor-specific binding compounds are disclosed including antibodies to $AT_2$ receptor epitopes. The invention provides $AT_2$ receptor-based pharmaceutical compositions and $AT_2$ receptor-based methods rot screening chemical libraries for regulators of cell growth/differentiation. In particular, the invention provides methods for identifying agonists and antagonists of the disclosed $AT_2$ receptor. Such compositions find broad utility in the treatment of cardiovascular disease, cancer, reproductive disease, etc.

5 Claims, 12 Drawing Sheets

```
                                                                    I
AT2R:  MKDNFSFAATSRNITSSLPFDNLNATGTNESAFNQSHKPADKH-LEAIPVLYYMIFVIGFA  60

AT1aR:                      MALNSSAEDGIKRIQDDQPKAGRHSYIFVMIPILYSIIFVVGIF  44

II
AT2R:  VNIVVVSLFCCQKGPKKVSSIYIFNLAVADLLLLATLPLWATYYSYRYDMLFGPVMCKVF  120

AT1aR: GNSLVVIVIYFYMKLKTVASVFLLNLALADLCFLLTLPLWAVYTAMEYRMPFGNHLCKIA  104

III                                 IV
AT2R:  GSFLTLNMFASIFFIICMSVDRYQSVIYPFLSQ-RRNPWQASYVVPLVMCMACLSSLPTFY  180

AT1aR: SASVSFNLYASVFLLICLSIDRYLAIVHPMKSRLRRTMLVAKVTCIIINLMAGLASLPAVI  165

V
AT2R:  FRDVRTIEYLGVNACIMAFPPE-KYAQWSAGIALMKNILGFIIPLIFIATCYFGIRKHLLK  240

AT1aR: HRNVYFIENTNITVC--AFHYESRNSTLPIGLGLTKNILGFLFPFLIILTSYTLIWKALKK  224

VI                          VII
AT2R:  TNSYGKNRITRDQVLKMAAAVVLAFIICMLFFHVLTFLDALTWMGIINSQEVIAVICLAL  300

AT1aR: AYEIQKNKPRNDDIFRIIMAIVLFFFFSMVFHQIPTFLDVLIQLGVIHDQKISDIVCTAM  284

AT2R:  PFAILLGFTNSCVNFFLYCFVGNRFQQKLRSVFRVPITWLQGKRETMSCRKSSSLREMDT  360

AT1aR: PITICIAYFNNCLNFLFYQFLGKKFKKYFLQLLKY-IP-PKAKSHSSLSTKMSTLSYRPS  342

AT2R:  FVS                   363

AT1aR: DNMSSSAKKPASCFEVE    359
```

FIG. 1A

```
GlnGlnLysLeuArgSerValPheArgValProIleThrThrTrpLeuGlnGlyLysLysArgGluThrMetSerCysArg    350
                                                           #                    #
CAACAGAAGCTCCGCAGTGTGTTTAGAGTTCCCATTACTACTTGGCTCCAAGGCAAGAGAGAGACTATGTCTTGCAGA      1050

LysSerSerLeuArgGluMetAspThrPheValSer***                                              363
   #     #
AAAGGCAGTTCTCTTAGAGAAATGACACCTTTGTGTCTTAAATCTGTTAGTGGATGCATGTAATCAGCCTAGC          1125
CATTGGTTTGGAGGCCCACACAAATGATCTTAAGTGGCATCAGTATAATACAGTTCTTTGCTTTATCTAATCTT         1200
TACTTACTCCCCCGAGAACAGGAGTCAAGTAGAACTGTAAATCTTTATACTCCACCAGCTTTCAGTGATAGTGC         1275
CTTCTTTTGCTGTCCTTGGCATGAGATTGTCATATGTGAGCTAGAATCTATAATCTAGAAGTATCTGGGGAAT         1350
TATCCCAACTTATAATTAACAACAAATTATGAGTGGTGATTTGACATCTCAGACTTCTCCCTGGAAAATGCTGGC        1425
ATTTCTTAGTGGAGTTTTTTGTCCATTTCATCAGATTTCTTTTTCTTGAACAAAGGCCAATTAAACTTCTTA          1500
TACTATCCAACCATATGATATAGCATGAGAGGTGAGCACTAAGTTTAGCATGAATATCTTCTATATATGCCAT         1575
AGGTTGGTAGTGGCTTATTCAGTCTTCTAGTATAGAGTTTCTCCTTTAAAGAATTGTAAGTTGTGTTCCTTTT         1650
CCATTTCACTCAAGTAGCTATATTCTACAGCTGAGCAGATCTAGAAACTGTAAAACAGAACTGCAATGAAAAGTA       1725
ACACATCTGTCTTAGCTTATTCTGCAGTTATAGAAAGTACACACTATTAGTAAAATTTTCATCCATTTGACTCT        1800
TTTTAGTATCCACAAAACTGAATATACACTTTGAAAATTTTCATGACACTGTATTATGCTAAAGGTCACTTTTTAAC     1875
TCTGATGATTTTGAATACAACAACAAAACACTGTATTATGACTGAGTTTAATTATTCATGCTTTTTTGTTCTGGGCTTCGT 1950
CTTTGAACATGGTGCTTTGATTCTTTGACCCTGAAAAAGAGAGCATTCTTTAACTTGTTGTAATAAAGTGCAAACTGGC    2025
CCCAAAATATCTCTTTGACCCTGAAAAAGAGAGCATTCTTTAACTTGTTGTAATAAAGTGCAAACTGGC               2100
ATGGGAAAAAGGTTATGTCAGAGACTGGAAGTTTGATGCCTTCTTGGGGTAAACAGACCCAGCAAATGGCAAGTTTG      2175
GTGTCCAACAAGGAACTGTCAGAGAACAAAGACTCCCTGGGAGTAGTTTGAATCTGCATTTCTGGGCACAGTTCC        2250
AGAATGTATAAGAGTCTGTGAAGGTGATTTAAAGCAAGCCACAGTTCCACAGAACTCATTCTTAACACGAGTACAT       2325
CTCTTACATTAGAGGAATATAATACCTGAAGCTGTGTTACCTAAAGTTTACTCAAACTTCTCAATAAATATTAAT        2400
TCAGAAGTTAAAGATGTCATTCTCTGCCTGTCCCTGTCCCATATTATACCAGTTCACCTAAGACCTTCCTGGATTGATGCT 2475
GACCTATGAGGTAGATTCAAAGTTCTGGAACTTAACATTTCGTCAGATTTCATGTTATTCATGTTAATTTTAGTAAAAACAAATAGCTAAAT 2550
CTCTCATACCCCTCCTTGGAAACCCTGATTTCATTCATGTTATTCATGTTAATTTTAGTAAAAACAAATAGCTAAAT    2625
ATGTAATCAGTTATGATGTCTTGTGTTTAAGCAATTTTACACAAATCTCGTAAAATAAAATCATTACTGGGAAAA      2700
AAAAAAAAAAAAAAAAAAAAAAAAAAAAAAA                                                    2731
```

FIG. 1B

```
                                                                          I
MOUSE AT2R  : MKDNFSFAATSRNITSSRPFDNLNATGTNESAFNCSHKPSDKH-LEAIPVLYYMIFVIGFA   60
RAT AT2R    : ..........L.............A...............................       60
MOUSE AT1aR : MALNSSTED.IKRIQDD.PRAGRHSYIFVM..T...SI...V.IF                    44

MOUSE AT2R  : VNIVVVSLFCCQKGPKKVSSIYIFNLALADLLLLATLPLWATYYSYRYDWLFGPVMCKVF   120
RAT AT2R    : .............................V..............................   120
MOUSE AT1aR : G.SL...IVIYFYMKL.T.A.VFLL........CF.L........V.TAME.R.P..NHL..IA   104
                                          III
MOUSE AT2R  : GSFLTLNMFASIFFITCMSVDRYQSVIYPFLSQ-RRNPWQASYVVPLVWCMACLSSLPTFY   180
RAT AT2R    : .............................................................   180
MOUSE AT1aR : SASVSF.LY..V.LL...L.I...LAIVH.MK.RL..TMLV.KVTCIII.L..G.A...AVI   165
                                                         V
MOUSE AT2R  : FRDVRTIEYLGVNACIMAFPPE-KYAQWSAGIALMKNILGFIIPLIFIATCYFGIRKHLLK   240
RAT AT2R    : .............................................................   240
MOUSE AT1aR : H.N.YF..NTNITV.--..HY..SRNSTLPI.LG.T......LF.FLI.L.S.TL.W.A.K.   224
                                   VI                              VII
MOUSE AT2R  : TNSYGKNRITRDQVLKMAAAVVLAFIICWLPFHVLTFLDALTWMGIINSCEVIAVIDLAL   300
RAT AT2R    : .............................................................   300
MOUSE AT1aR : AYEIQ..KPRN.DIFRIIM.I..F.FFS.V.HQIF.....V.IQL.V.HD.KIADIV.T.M   284

MOUSE AT2R  : PFAILLGFTNSCVNPFLYCFVGNRFQQKLRSVFRVPITWLQGKRETMSCRKGSSLREMDT   360
RAT AT2R    : ...............................S.............................   360
MOUSE AT1aR : .IT.CIAYF.N.L..LF.G.L.KK.KKYFLQLLKY--PPKA.SHSSLST.M.T.SYRPS     342

MOUSE AT2R  : FVS                363
RAT AT2R    : ...                363
MOUSE AT1aR : DNMSSAAKKPASCSSEVE 359
```

FIG. 3

```
-149       GGGGATGGAGCGAGCACAGAATTGAAAGCTTTCTTCAGCCTGCATTTAAGGAGTGCGTGTGGGAAGCTCAGTA
       AGCTGATTATGATAACTGCTTTAAACACTGCCAACTAAAAGAGTGTAAGGATTGGGAGTCTCTGACAGTTCAAT        -1
                    *                                         *
       MetLysAspAsnPheSerAlaAlaThrSerArgAsnIleThrSerLeuProPheAspAsnLeuAsnAla              25
       ATGAAGGACAACTTCAGTTTTGCTGCCACAAGCAGAAACATTACCAGCAGTCTCCTTTTGATAATCTCAACGCA          75
                    *
       ThrGlyThrAsnGluSerAlaPheAsnCysSerHisLysProAlaAspLysHisLeuGluAlaIleProValLeu        50
       ACTGGCACCAATGAGTCCGCATTTAACTGCTCACACAAACCGGCAGATAAGCATTTGGAAGCAATTCCTGTTCTC         150
                                    *
                 I
       TyrTyrMetIlePheValIleGlyPheAlaValIleGlyPheAlaValValAsnIleValValSerLeuPheCysCysGlnLysGlyPro   75
       TACTACATGATTTTTGTGATTGGTTTTGCTGTTAACATTGTTGTGTCTCACTGTTTTGTGTCAAAAGGGCCCT           225
                                        II
       LysLysValSerSerIleTyrIlePheAsnLeuAlaValAlaAlaAspLeuLeuLeuLeuAlaThrLeuProLeuTrp      100
       AAAAAGGTGTCCAGCATTTACATCTTCAATCTGGCTGTGGCTGCTGACTTACTCCCTTTTGGCAACCCTTCCTCTGG       300
                                                                                III
       AlaThrTyrTyrSerTyrArgTyrAspTyrArgPheLeuProValMetCysLysValPheGlySerPheLeuThr        125
       GCAACCTATTACTCTTATAGATATGACTGGCTCTTTGGACCTGTGATGTGCAAAGTGTTTGGTTCTTTTCTGACC         375
                III
       LeuAsnMetPheAlaSerIlePhePheIleThrCysMetSerValAspArgTyrGlnSerValIleTyrProPhe         150
       CTGAACATGTTTGCAAGCATTTTTTTATTACGTGCATGAGTGTTGATAGGTACCAATGGTTATCTACCCTTTT           450
              #                                                     IV
       LeuSerGlnArgArgAsnProTrpGlnAlaSerTyrValValProLeuValTrpCysMetAlaCysLeuSerSer        175
       CTGTCTCAGAGAAGAAATCCCTGGCAAGCATCTTATGTAGTTCCCCTTGTTTGGTGTATGGCTTGTCTGTCCTCA         525
       LeuProThrPheTyrPheArgArgAspValArgThrIleGluTyrLeuGlyValAlaAsnAlaCysIleMetAlaPhePro  200
       TTGCCAACATTTTATTTCCGAGATGTCAGAACCATTGAATACTTAGGTGTGAATGCTTGTATTATGGCTTTCCCA         600
                                                                    V
       ProGluLysTyrAlaGlnTrpSerArgLysHisLeuLeuLysThrAsnSerTyrGlyLysHisLeuLeuProLeuIle     225
       CCTGAGAAATATGCTCAGTGGTCTCGTGGCTCTGCTGGGATTGCTTAATGAAAAATATTCTTGGCTTTATCATTCCTTTAATA 675
       PheIleAlaThrCysTyrPheGlyIleArgLysHisLeuLeuLysThrAsnSerTyrGlyLysAsnArgIleThr         250
       TTCATAGCAACGTGTTACTTTGGAATCAGAAAACATCTGCTGAAGACCAATAGCTATGGGAAGAACAGAATTACC         750
                                                                            VI
       ArgAspGlnValLeuLeuLysMetAlaAlaAlaValLeuAlaPheIleIleCysTrpLeuProPheHisValLeu         275
       CGTGACCAAGTCTTGAAGATGGCAGCTGCTGTGTTGGCATTCATCATTTGCTGGCTTCCCTTCCATGTTCTG            825
```

FIG. 6B

```
                                                                    VII
ThrPheLeuAspAlaLeuThrTrpMetGlyIleIleIleAsnSerCysGluValValIleAlaValIleAspLeuAlaLeu
ACCTTCTTGGATGCTCTGACCTGGATGGGTATCATTATTAATAGCTGTGAAGTAGCAGTCATTGACCTGCACTT          300
                                                                                    900

ProPheAlaIleLeuLeuGlyPheThrAsnSerCysValAsnProPheLeuTyrCysPheValGlyAsnArgPhe
CCTTTTGCCATCCTCCTGGGATTCACCAACAGCTGTGTTAATCCCTTCCTGTATTGTTTCGTTGGAAACCGCTTC        325
         #                                                                #        975

GlnGlnLysLeuArgSerValPheArgValProIleThrTrpLeuGlnGlyLysArgGluThrMetSerCysArg
CAACAGAAGCTCCGTAGTGTTTTTAGAGTTCCCATTACTTGGCTCCAAGGCAAGAGAGACTATGTCTTGCCGA          350
         #  #                                                                      1050

LysSerSerLeuArgGluMetAspThrPheValSer***
AAAAGCAGTTCTCTTAGAGAAATGGACACCTTTGTGTCTTAAATCTGTTAGTGGGATGCATGTAATCAGCCTAGC       363
                                                                                   1125

AATGGTTTGGAGGCCCACACAAATGATCTTAAGTGACATCAGTATATAATATAATTCTTTGCTTTTTCTAATCTTT       1200
ATTACTCCCCCAGAACAGGAAATAATCAGTATAATTATAAACCTTTATACTCCACCAGCTTTCAGTGATAGTGCCT       1275
TCTTTTTCTGGTCCGTTGGCAGGAGATTGTCATATGTGAGCTTTATCTATAATCTAGAAGTATCTGGGGAATTA        1350
TCTCGACTTATAATTAAAAACAAATTAGAGTGATGATATATTTTTTCATCTGATATTGTCTCGGATTTCTCCCTGGATTTCTCCCTGGATTCCCCTGAAAAATGCTGGCAT 1425
TTCTTAGTGGAGTTTATGTCCATTTCATCTCGATATTTTTTCTCCTTGAACAAGGCCAATTTGAACTTCTTAC         1500
ACTTTCCAACCATATGATGATAGAGCATGAGAGTGGGCACTAGAGTTAGCATGCTATACCCTTCTATATATGCCATA     1575
GGTTGGTAGTGCTTATTCAGTCTTTTTACTAGTCTTCCCTTTAAAGAAAATTATAAGTTGTGTTCCTTTTC            1650
CATTTCACTCAAGTAGTATAGCTTTCTAAAACCACTGAGTAGATCTAAAACTGAGTAGAATGTGTTAAATCACAC        1725
TTCCTATTAGCTTATCCTTGAAGTTATAGAGCGCACGCTATTAGTAGTAAAACAGAACTACCCTGAAAAAGTATTT       1800
TATTAACCACAAAACTGAATATACACTGGAAAACTTTCATCCATTTGACTATTGTTTCAAGTTTTCTATTCT           1875
CTTCTGATGATTTTGAACACGACCAACAAAACTGTATTATTAGATGACATAAAGGTCACTTTTTACATTTTTA          1950
ACCTTTGAACATGGTGCTTTGATATATTCTATGGTGACTTGAGTTTAATTATTCATGCTTTTGTTCTGGGCTGC         2025
GTCCAAAATATCTTTTGACCCTGAAAAAGAGAGGATTCTTTAATTCTTTAGCTTTATAATAAACTGCACACTG          2100
GCATAGGAAAAGGTTATGTCAGAATGGAAGTTTGATGCCCTCTTGGGACCAAACAGACCCAGAGAACGGCAAGT         2175
TTGGTGTCCAACAAGGAACTTGTCAGAACAAGGCCCCTGGAGTATTTTGAATCTGCATTTCTGGGCACAGTT           2250
CCAGAATATATAAGAGTCTGTGGAGGTGATTAAATCAAGCCCAGGTCCACTAAGTCATTCTCAACACGAGTAC          2325
ATCTCTTACATTAGAGGAATATAATCCCGGAAACTGAGTCACTCAAACTTCACAATAAGTATTA                   2400
ATTCAAACGTTCAAAATGCCATTCTCTTACTGCCCCATATTATACCAGGTCGCCTGAGACCTTTCTGGACTGATA        2475
ATGACCTCGAGGTAGATTTAAGTTTTGGGAACTTAACATTTCTGTCAGATTTCAGGCTTTTTGGTTGGAAGAA         2550
TCCTCTCATACCCCTTCCTTGGAAAACCCTGATTTCATGTATTCATATTATGTGTTACTAAGATCAAGTAGCTAA        2625
ATATATAATCAGTTATGATTTGTGTTTTAAGTAATTTACACAACATCTCATAAAAATAAAATCATTATTGGGA          2700
AAAAAAAAAAAAAAAAAAAAAAAAAA                                                         2735
```

FIG. 6B-1

```
                                                           ┌─────────I──┐
AT2R:  MKDNFSFAATSRNITSSLPFDNLNATGTNESAFNQSHKPADKH-LEAIPVLYYMIFVIGFA     60

AT1aR:                 MALNSSAEDGIKRIQDDQPKAGRHSYIFVMIPILYSIIFVVGIF      44

┌──────────┐            ┌─────────II────────┐                ┌
AT2R:  VNIVVVSLFCCQKGPKKVSSIYIFNLAVADLLLLATLPLWATYYSYRYDMLFGPVMCKVF    120

AT1aR: GNSLVVIVIYFYMKLKTVASVFLLNLALADLCFLLTLPLWAVYTAMEYRMPFGNHLCKIA    104

┌──────III────────┐                     ┌──────IV────────┐
AT2R:  GSFLTLNMFASIFFIICMSVDRYQSVIYPFLSQ-RRNPWQASYVVPLVMCMACLSSLPTFY   180

AT1aR: SASVSFNLYASVFLLICLSIDRYLAIVHPMKSRLRRTMLVAKVTCIIINLMAGLASLPAVI   165

┌──────────V──────────┐
AT2R:  FRDVRTIEYLGVNACIMAFPPE-KYAQWSAGIALMKNILGFIIPLIFIATCYFGIRKHLLK   240

AT1aR: HRNVYFIENTNITVC--AFHYESRNSTLPIGLGLTKNILGFLPFLIILTSYTLIWKALKK    224

┌──────────VI─────────┐        ┌─────────VII-
AT2R:  TNSYGKNRITRDQVLKMAAAVVLAFIICMLFFHVLTFLDALTWMGIINSQEVIAVICLAL    300

AT1aR: AYEIQKNKPRNDDIFRIIMAIVLFFFFSMVFHQIPTFLDVLIQLGVIHDQKISDIVCTAM    284

──────────┐
AT2R:  PFAILLGFTNSCVNFFLYCFVGNRFQQKLRSVFRVPITWLQGKRETMSCRKSSSLREMDT    360

AT1aR: PITICIAYFNNCLNFLFYQFLGKKFKKYFLQLLKY-IP-PKAKSHSSLSTKMSTLSYRPS    342

AT2R:  FVS                 363

AT1aR: DNMSSSAKKPASCFEVE    359
```

FIG. 6C

```
rAT2R:   R-KHLLKTNSYGKNRITRDQVLK     256
mSSTR1:  R-MVALKAGWQQRKRSERKITL      271
rD3R:    RIYIVLRQR148PLREKKATQ       375 dFz:     RIRTVMKTDGKRTDKLERLMLR      471
rFZ-1:   RIRTIMKHDGTKTEKLEKLMVR      530
rFZ-2:   RIRTIMKHDGTKTEKLERLMVR      466
```

FIG. 6d

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 2862 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 132..1223

( x i ) SEQUENCE DESCRIPTION: SEQ ID NO:1:

```
CGGAACTGAA  AGCTTACTTC  AGCCTGCATT  TTAAGGAGTG  CATGCGGGAG  CTGAGTAAGC           60

TGATTTATGA  TAACTGCTTT  AAACACTGGC  AACTAAAAAG  GTGTAAGAAT  TTGGAGTTGC          120

TGCAGTTCAA  T ATG AAG GAC AAC TTC AGT TTT GCT GCC ACC AGC AGA AAC              170
              Met Lys Asp Asn Phe Ser Phe Ala Ala Thr Ser Arg Asn
                1               5                   10

ATT ACC AGC AGC CGT CCT TTT GAT AAT CTC AAC GCA ACT GGC ACC AAT                218
Ile Thr Ser Ser Arg Pro Phe Asp Asn Leu Asn Ala Thr Gly Thr Asn
     15                  20                  25

GAG TCC GCC TTT AAT TGC TCA CAC AAA CCA TCA GAT AAG CAT TTG GAA                266
Glu Ser Ala Phe Asn Cys Ser His Lys Pro Ser Asp Lys His Leu Glu
 30                  35                  40                  45

GCA ATT CCT GTT CTC TAC TAC ATG ATT TTT GTG ATT GGG TTT GCT GTT                314
Ala Ile Pro Val Leu Tyr Tyr Met Ile Phe Val Ile Gly Phe Ala Val
                 50                  55                  60

AAT ATT GTT GTG GTC TCA CTG TTT TGT TGT CAA AAG GGC CCT AAA AAG                362
Asn Ile Val Val Val Ser Leu Phe Cys Cys Gln Lys Gly Pro Lys Lys
             65                  70                  75

GTG TCC AGC ATT TAC ATC TTC AAT CTG GCC TTG GCT GAC TTA CTC CTT                410
Val Ser Ser Ile Tyr Ile Phe Asn Leu Ala Leu Ala Asp Leu Leu Leu
         80                  85                  90

TTG GCT ACC CTC CCT CTC TGG GCA ACC TAT TAC TCT TAT AGA TAT GAT                458
```

|     |     |     |     |     |     |     |     |     |     |     |     |     |     |     |     |
| --- | --- | --- | --- | --- | --- | --- | --- | --- | --- | --- | --- | --- | --- | --- | --- |
| Leu | Ala | Thr | Leu | Pro | Leu | Trp | Ala | Thr | Tyr | Tyr | Ser | Tyr | Arg | Tyr | Asp |
|     | 95  |     |     |     | 100 |     |     |     |     | 105 |     |     |     |     |     |

| TGG | CTT | TTT | GGA | CCT | GTG | ATG | TGC | AAA | GTG | TTT | GGT | TCT | TTT | CTG | ACT | 506 |
| --- | --- | --- | --- | --- | --- | --- | --- | --- | --- | --- | --- | --- | --- | --- | --- | --- |
| Trp | Leu | Phe | Gly | Pro | Val | Met | Cys | Lys | Val | Phe | Gly | Ser | Phe | Leu | Thr |     |
| 110 |     |     |     |     | 115 |     |     |     |     | 120 |     |     |     |     | 125 |     |

| CTG | AAC | ATG | TTT | GCA | AGC | ATT | TTT | TTT | ATT | ACC | TGC | ATG | AGT | GTC | GAT | 554 |
| --- | --- | --- | --- | --- | --- | --- | --- | --- | --- | --- | --- | --- | --- | --- | --- | --- |
| Leu | Asn | Met | Phe | Ala | Ser | Ile | Phe | Phe | Ile | Thr | Cys | Met | Ser | Val | Asp |     |
|     |     |     |     | 130 |     |     |     |     | 135 |     |     |     |     | 140 |     |     |

| AGG | TAC | CAA | TCG | GTC | ATC | TAC | CCT | TTT | CTG | TCT | CAA | AGA | AGG | AAT | CCC | 602 |
| --- | --- | --- | --- | --- | --- | --- | --- | --- | --- | --- | --- | --- | --- | --- | --- | --- |
| Arg | Tyr | Gln | Ser | Val | Ile | Tyr | Pro | Phe | Leu | Ser | Gln | Arg | Arg | Asn | Pro |     |
|     |     |     | 145 |     |     |     |     |     | 150 |     |     |     |     | 155 |     |     |

| TGG | CAA | GCA | TCT | TAT | GTA | GTT | CCC | CTT | GTT | TGG | TGT | ATG | GCT | TGT | CTA | 650 |
| --- | --- | --- | --- | --- | --- | --- | --- | --- | --- | --- | --- | --- | --- | --- | --- | --- |
| Trp | Gln | Ala | Ser | Tyr | Val | Val | Pro | Leu | Val | Trp | Cys | Met | Ala | Cys | Leu |     |
|     |     | 160 |     |     |     |     | 165 |     |     |     |     | 170 |     |     |     |     |

| TCC | TCA | TTG | CCA | ACA | TTT | TAT | TTC | CGG | GAT | GTC | AGA | ACC | ATT | GAA | TAC | 698 |
| --- | --- | --- | --- | --- | --- | --- | --- | --- | --- | --- | --- | --- | --- | --- | --- | --- |
| Ser | Ser | Leu | Pro | Thr | Phe | Tyr | Phe | Arg | Asp | Val | Arg | Thr | Ile | Glu | Tyr |     |
|     | 175 |     |     |     |     | 180 |     |     |     |     | 185 |     |     |     |     |     |

| TTA | GGT | GTG | AAT | GCT | TGT | ATT | ATG | GCT | TTC | CCA | CCC | GAG | AAA | TAT | GCT | 746 |
| --- | --- | --- | --- | --- | --- | --- | --- | --- | --- | --- | --- | --- | --- | --- | --- | --- |
| Leu | Gly | Val | Asn | Ala | Cys | Ile | Met | Ala | Phe | Pro | Pro | Glu | Lys | Tyr | Ala |     |
| 190 |     |     |     |     | 195 |     |     |     |     | 200 |     |     |     |     | 205 |     |

| CAG | TGG | TCT | GCT | GGG | ATT | GCC | TTA | ATG | AAA | AAT | ATT | CTT | GGC | TTT | ATT | 794 |
| --- | --- | --- | --- | --- | --- | --- | --- | --- | --- | --- | --- | --- | --- | --- | --- | --- |
| Gln | Trp | Ser | Ala | Gly | Ile | Ala | Leu | Met | Lys | Asn | Ile | Leu | Gly | Phe | Ile |     |
|     |     |     |     | 210 |     |     |     |     | 215 |     |     |     |     | 220 |     |     |

| ATT | CCT | TTA | ATA | TTC | ATA | GCA | ACG | TGT | TAC | TTT | GGA | ATC | AGA | AAA | CAT | 842 |
| --- | --- | --- | --- | --- | --- | --- | --- | --- | --- | --- | --- | --- | --- | --- | --- | --- |
| Ile | Pro | Leu | Ile | Phe | Ile | Ala | Thr | Cys | Tyr | Phe | Gly | Ile | Arg | Lys | His |     |
|     |     |     | 225 |     |     |     |     | 230 |     |     |     |     | 235 |     |     |     |

| CTG | CTG | AAG | ACT | AAT | AGC | TAT | GGG | AAG | AAC | AGA | ATT | ACC | CGT | GAC | CAA | 890 |
| --- | --- | --- | --- | --- | --- | --- | --- | --- | --- | --- | --- | --- | --- | --- | --- | --- |
| Leu | Leu | Lys | Thr | Asn | Ser | Tyr | Gly | Lys | Asn | Arg | Ile | Thr | Arg | Asp | Gln |     |
|     |     | 240 |     |     |     |     | 245 |     |     |     |     | 250 |     |     |     |     |

| GTC | CTG | AAG | ATG | GCA | GCT | GCT | GTT | GTG | TTG | GCA | TTC | ATC | ATT | TGC | TGG | 938 |
| --- | --- | --- | --- | --- | --- | --- | --- | --- | --- | --- | --- | --- | --- | --- | --- | --- |
| Val | Leu | Lys | Met | Ala | Ala | Ala | Val | Val | Leu | Ala | Phe | Ile | Ile | Cys | Trp |     |
|     | 255 |     |     |     |     | 260 |     |     |     |     | 265 |     |     |     |     |     |

| CTT | CCC | TTC | CAT | GTT | CTG | ACC | TTC | TTG | GAT | GCT | CTG | ACC | TGG | ATG | GGT | 986 |
| --- | --- | --- | --- | --- | --- | --- | --- | --- | --- | --- | --- | --- | --- | --- | --- | --- |
| Leu | Pro | Phe | His | Val | Leu | Thr | Phe | Leu | Asp | Ala | Leu | Thr | Trp | Met | Gly |     |
| 270 |     |     |     |     | 275 |     |     |     |     | 280 |     |     |     |     | 285 |     |

| ATC | ATT | AAT | AGC | TGT | GAA | GTT | ATA | GCA | GTC | ATT | GAC | CTG | GCA | CTT | CCT | 1034 |
| --- | --- | --- | --- | --- | --- | --- | --- | --- | --- | --- | --- | --- | --- | --- | --- | --- |
| Ile | Ile | Asn | Ser | Cys | Glu | Val | Ile | Ala | Val | Ile | Asp | Leu | Ala | Leu | Pro |     |
|     |     |     |     | 290 |     |     |     |     | 295 |     |     |     |     | 300 |     |     |

| TTT | GCC | ATC | CTC | CTG | GGA | TTC | ACC | AAC | AGC | TGT | GTT | AAT | CCC | TTC | CTG | 1082 |
| --- | --- | --- | --- | --- | --- | --- | --- | --- | --- | --- | --- | --- | --- | --- | --- | --- |
| Phe | Ala | Ile | Leu | Leu | Gly | Phe | Thr | Asn | Ser | Cys | Val | Asn | Pro | Phe | Leu |     |
|     |     |     | 305 |     |     |     |     | 310 |     |     |     |     | 315 |     |     |     |

| TAT | TGT | TTT | GTT | GGA | AAC | CGC | TTC | CAA | CAG | AAG | CTC | CGC | AGT | GTG | TTT | 1130 |
| --- | --- | --- | --- | --- | --- | --- | --- | --- | --- | --- | --- | --- | --- | --- | --- | --- |
| Tyr | Cys | Phe | Val | Gly | Asn | Arg | Phe | Gln | Gln | Lys | Leu | Arg | Ser | Val | Phe |     |
|     |     | 320 |     |     |     |     | 325 |     |     |     |     | 330 |     |     |     |     |

| AGA | GTT | CCC | ATT | ACT | TGG | CTC | CAA | GGC | AAG | AGA | GAG | ACT | ATG | TCT | TGC | 1178 |
| --- | --- | --- | --- | --- | --- | --- | --- | --- | --- | --- | --- | --- | --- | --- | --- | --- |
| Arg | Val | Pro | Ile | Thr | Trp | Leu | Gln | Gly | Lys | Arg | Glu | Thr | Met | Ser | Cys |     |
|     |     | 335 |     |     |     |     | 340 |     |     |     |     | 345 |     |     |     |     |

| AGA | AAA | GGC | AGT | TCT | CTT | AGA | GAA | ATG | GAC | ACC | TTT | GTG | TCT | TAAATCTGTT | 1230 |
| --- | --- | --- | --- | --- | --- | --- | --- | --- | --- | --- | --- | --- | --- | --- | --- |
| Arg | Lys | Gly | Ser | Ser | Leu | Arg | Glu | Met | Asp | Thr | Phe | Val | Ser |     |     |
| 350 |     |     |     |     | 355 |     |     |     |     | 360 |     |     |     |     |     |

| AGTGGGATGC | ATGTAATCAG | CCTAGCCATT | GGTTTGGAGG | CCCACACAAA | TGATCTTTAA | 1290 |
| --- | --- | --- | --- | --- | --- | --- |
| GTGGCATCAG | TATAATACAG | TTCTTTGCTT | TATCTAATCT | TTACTTACTC | CCCCGAGAAC | 1350 |
| AGGAAGTCAA | GTAGAACTGT | AAATCTTTAT | ACTCCACCAG | CTTTCAGTGA | TAGTGCCTTC | 1410 |
| TTTTGCTGGT | CCTTTGGCAT | GAGATTGTCA | TATGTGAGCT | AGATCTATAA | TCTAGAAGTA | 1470 |
| TCTGGGGGAA | TTATCCCAAC | TTATAATTAA | CAACAAATTA | TGAGTGGTGA | TTTGACATCT | 1530 |
| CAGACTTCTC | CCTGGAAAAT | GCTGGCATTT | CTTAGTGGAG | TTTTTTGTCC | ATTTTCATCA | 1590 |
| GATTTCTTTT | TTCTTGAACA | AAGGCCAATT | TAAACTTCTT | ATACTATCCA | ACCATATGAT | 1650 |

| | | | | | | |
|---|---|---|---|---|---|---|
| ATAGCATGAG | AGGTGAGCAC | TAAGTTTAGC | ATGATATACT | CTTCTATATA | TGCCATAGGT | 1710 |
| TGGTAGTGGC | TTATTCAGTC | TCTAGGTATA | GAGTTTCTCC | TTTTAAAGAA | ATTGTAAGTT | 1770 |
| GTGTTCCTTT | TCCATTTCAC | TCAAGTATAG | CTTTTGTACT | TATTCTACAG | CTACACACTG | 1830 |
| AGCAGATCTA | GAATGTAGAT | TAAATCACAC | ATCTGTCTTA | GCTTATTCTT | GCAGTTATAG | 1890 |
| AAAGTACACT | ATTTAGTAAA | ACAGAACTGC | AATGAAAAGT | ATTTAGTAT | CCACAAAACT | 1950 |
| GAATATACAC | TTTGAAAATT | TTTCATCCAT | TTTGACTCTT | GTTATTCTA | TTCTCTTCTG | 2010 |
| ATGATTTTG | AATACAACAA | CAAACACTG | TATTATGACA | CTACGTAAAG | GTCACTTTTT | 2070 |
| AAATTTTAA | CCTTTTGAAC | ATGGTGCTTT | GATATATTCA | ATGATGACTT | GAGTTTAATT | 2130 |
| ATTCATGCTT | TTGTTCTGGG | CTTCGTCCCA | AAATATCTCT | TTGACCCTGA | AAAGAGAGC | 2190 |
| ATTCTTTAAT | TCTTTAACTT | TGTAATAAAG | TGCAAACTGG | CATGGGAAAA | GGTTATGTCA | 2250 |
| GACTGGAAGT | TTGATGCCTT | CTTGGGGGTA | AACAGACCCA | GCAAATGGCA | AGTTTGGTGT | 2310 |
| CCAACAAGGA | ACTTGTCAGA | ACAAGACTC | CCTGGGGAGT | AGTTTGAATC | TGCATTTCTG | 2370 |
| GGCACAGTTC | CAGAATGTAT | AAGAGTCTGT | GAAGGTGATT | TAAAGCAAGC | CCAGGTCCAC | 2430 |
| AGAACTCATT | CTTAACACGA | GTACATCTCT | TACATTAGAG | GAATATAATA | CCTGAAGCTG | 2490 |
| TGTTACCTAA | AGTTTACTCA | AACTTCTCAA | TAAATATTAA | TTCAGAAGTT | AAAGATGTCA | 2550 |
| TTCTCTGCCT | GTCCCATATT | ATACCAGGTC | ACCTAAGACC | TTCCTGGATT | GATGCTGACC | 2610 |
| TATGAGGTAG | ATTCAAAGTT | CTGGGAACTT | AACATTTCTG | TCAGATTCCA | GGCGTTTAG | 2670 |
| GTTGAAGAAT | CCTCTCATAC | CCCTTCCTTG | GAAAACCCTG | ATTTCATGTA | TTCATGTTAA | 2730 |
| TTTTAGTAA | AAACAAATAG | CTAAATATGT | AATCAGTTAT | GACTTTGTGT | TTTAAGCAAT | 2790 |
| TTTACACAAA | ATCTCGTAAA | ATAAAATCAT | TACTGGGAAA | AAAAAAAAA | AAAAAAAAA | 2850 |
| AAAAAAAAA | AA | | | | | 2862 |

( 2 ) INFORMATION FOR SEQ ID NO:2:

( i ) SEQUENCE CHARACTERISTICS:
        ( A ) LENGTH: 363 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Asp Asn Phe Ser Phe Ala Ala Thr Ser Arg Asn Ile Thr Ser
 1               5                  10                  15

Ser Arg Pro Phe Asp Asn Leu Asn Ala Thr Gly Thr Asn Glu Ser Ala
            20                  25                  30

Phe Asn Cys Ser His Lys Pro Ser Asp Lys His Leu Glu Ala Ile Pro
        35                  40                  45

Val Leu Tyr Tyr Met Ile Phe Val Ile Gly Phe Ala Val Asn Ile Val
    50                  55                  60

Val Val Ser Leu Phe Cys Cys Gln Lys Gly Pro Lys Lys Val Ser Ser
65                  70                  75                  80

Ile Tyr Ile Phe Asn Leu Ala Leu Ala Asp Leu Leu Leu Leu Ala Thr
                85                  90                  95

Leu Pro Leu Trp Ala Thr Tyr Tyr Ser Tyr Arg Tyr Asp Trp Leu Phe
                100                 105                 110

Gly Pro Val Met Cys Lys Val Phe Gly Ser Phe Leu Thr Leu Asn Met
            115                 120                 125

Phe Ala Ser Ile Phe Phe Ile Thr Cys Met Ser Val Asp Arg Tyr Gln
```

|     |     |     |     |     | 130 |     |     |     | 135 |     |     |     |     | 140 |     |
| --- | --- | --- | --- | --- | --- | --- | --- | --- | --- | --- | --- | --- | --- | --- | --- |
| Ser<br>145 | Val | Ile | Tyr | Pro | Phe<br>150 | Leu | Ser | Gln | Arg<br>155 | Arg | Asn | Pro | Trp | Gln | Ala<br>160 |
| Ser | Tyr | Val | Val | Pro<br>165 | Leu | Val | Trp | Cys | Met<br>170 | Ala | Cys | Leu | Ser | Ser<br>175 | Leu |
| Pro | Thr | Phe | Tyr<br>180 | Phe | Arg | Asp | Val | Arg<br>185 | Thr | Ile | Glu | Tyr | Leu<br>190 | Gly | Val |
| Asn | Ala | Cys<br>195 | Ile | Met | Ala | Phe | Pro<br>200 | Pro | Glu | Lys | Tyr | Ala<br>205 | Gln | Trp | Ser |
| Ala | Gly<br>210 | Ile | Ala | Leu | Met | Lys<br>215 | Asn | Ile | Leu | Gly | Phe<br>220 | Ile | Ile | Pro | Leu |
| Ile<br>225 | Phe | Ile | Ala | Thr | Cys<br>230 | Tyr | Phe | Gly | Ile | Arg<br>235 | Lys | His | Leu | Leu | Lys<br>240 |
| Thr | Asn | Ser | Tyr | Gly<br>245 | Lys | Asn | Arg | Ile | Thr<br>250 | Arg | Asp | Gln | Val | Leu<br>255 | Lys |
| Met | Ala | Ala | Ala<br>260 | Val | Val | Leu | Ala | Phe<br>265 | Ile | Ile | Cys | Trp | Leu<br>270 | Pro | Phe |
| His | Val | Leu<br>275 | Thr | Phe | Leu | Asp | Ala<br>280 | Leu | Thr | Trp | Met | Gly<br>285 | Ile | Ile | Asn |
| Ser | Cys<br>290 | Glu | Val | Ile | Ala | Val<br>295 | Ile | Asp | Leu | Ala | Leu<br>300 | Pro | Phe | Ala | Ile |
| Leu<br>305 | Leu | Gly | Phe | Thr | Asn<br>310 | Ser | Cys | Val | Asn | Pro<br>315 | Phe | Leu | Tyr | Cys | Phe<br>320 |
| Val | Gly | Asn | Arg | Phe<br>325 | Gln | Gln | Lys | Leu | Arg<br>330 | Ser | Val | Phe | Arg | Val<br>335 | Pro |
| Ile | Thr | Trp | Leu<br>340 | Gln | Gly | Lys | Arg | Glu<br>345 | Thr | Met | Ser | Cys | Arg<br>350 | Lys | Gly |
| Ser | Ser | Leu<br>355 | Arg | Glu | Met | Asp | Thr<br>360 | Phe | Val | Ser |     |     |     |     |     |

( 2 ) INFORMATION FOR SEQ ID NO:3:

( i ) SEQUENCE CHARACTERISTICS:
        ( A ) LENGTH: 363 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

| Met<br>1 | Lys | Asp | Asn | Phe<br>5 | Ser | Phe | Ala | Ala | Thr<br>10 | Ser | Arg | Asn | Ile | Thr<br>15 | Ser |
| --- | --- | --- | --- | --- | --- | --- | --- | --- | --- | --- | --- | --- | --- | --- | --- |
| Ser | Leu | Pro | Phe<br>20 | Asp | Asn | Leu | Asn | Ala<br>25 | Thr | Gly | Thr | Asn | Glu<br>30 | Ser | Ala |
| Phe | Asn | Cys<br>35 | Ser | His | Lys | Pro | Ala<br>40 | Asp | Lys | His | Leu | Glu<br>45 | Ala | Ile | Pro |
| Val | Leu<br>50 | Tyr | Tyr | Met | Ile | Phe<br>55 | Val | Ile | Gly | Phe | Ala<br>60 | Val | Asn | Ile | Val |
| Val<br>65 | Val | Ser | Leu | Phe | Cys<br>70 | Cys | Gln | Lys | Gly | Pro<br>75 | Lys | Lys | Val | Ser | Ser<br>80 |
| Ile | Tyr | Ile | Phe | Asn<br>85 | Leu | Ala | Val | Ala | Asp<br>90 | Leu | Leu | Leu | Leu | Ala<br>95 | Thr |
| Leu | Pro | Leu | Trp<br>100 | Ala | Thr | Tyr | Tyr | Ser<br>105 | Tyr | Arg | Tyr | Asp | Trp<br>110 | Leu | Phe |
| Gly | Pro | Val | Met<br>115 | Cys | Lys | Val | Phe | Gly<br>120 | Ser | Phe | Leu | Thr | Leu<br>125 | Asn | Met |

```
Phe Ala Ser Ile Phe Phe Ile Thr Cys Met Ser Val Asp Arg Tyr Gln
    130             135             140

Ser Val Ile Tyr Pro Phe Leu Ser Gln Arg Arg Asn Pro Trp Gln Ala
145             150                 155                     160

Ser Tyr Val Val Pro Leu Val Trp Cys Met Ala Cys Leu Ser Ser Leu
                165             170                     175

Pro Thr Phe Tyr Phe Arg Asp Val Arg Thr Ile Glu Tyr Leu Gly Val
                180             185                 190

Asn Ala Cys Ile Met Ala Phe Pro Pro Glu Lys Tyr Ala Gln Trp Ser
        195             200                 205

Ala Gly Ile Ala Leu Met Lys Asn Ile Leu Gly Phe Ile Ile Pro Leu
    210             215                 220

Ile Phe Ile Ala Thr Cys Tyr Phe Gly Ile Arg Lys His Leu Leu Lys
225             230                 235                     240

Thr Asn Ser Tyr Gly Lys Asn Arg Ile Thr Arg Asp Gln Val Leu Lys
                245             250                     255

Met Ala Ala Ala Val Val Leu Ala Phe Ile Ile Cys Trp Leu Pro Phe
            260             265             270

His Val Leu Thr Phe Leu Asp Ala Leu Thr Trp Met Gly Ile Ile Asn
        275             280             285

Ser Cys Glu Val Ile Ala Val Ile Asp Leu Ala Leu Pro Phe Ala Ile
    290             295             300

Leu Leu Gly Phe Thr Asn Ser Cys Val Asn Pro Phe Leu Tyr Cys Phe
305             310             315                     320

Val Gly Asn Arg Phe Gln Gln Lys Leu Arg Ser Val Phe Arg Val Pro
            325                 330             335

Ile Thr Trp Leu Gln Gly Lys Arg Glu Thr Met Ser Cys Arg Lys Ser
            340             345             350

Ser Ser Leu Arg Glu Met Asp Thr Phe Val Ser
            355             360
```

( 2 ) INFORMATION FOR SEQ ID NO:4:

( i ) SEQUENCE CHARACTERISTICS:
        ( A ) LENGTH: 359 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met Ala Leu Asn Ser Ser Ala Glu Asp Gly Ile Lys Arg Ile Gln Asp
1               5               10                  15

Asp Cys Pro Lys Ala Gly Arg His Ser Tyr Ile Phe Val Met Ile Pro
            20              25              30

Thr Leu Tyr Ser Ile Ile Phe Val Val Gly Ile Phe Gly Asn Ser Leu
        35              40              45

Val Val Ile Val Ile Tyr Phe Tyr Met Lys Leu Lys Thr Val Ala Ser
        50              55              60

Val Phe Leu Leu Asn Leu Ala Leu Ala Asp Leu Cys Phe Leu Leu Thr
65              70              75              80

Leu Pro Leu Trp Ala Val Tyr Thr Ala Met Glu Tyr Arg Trp Pro Phe
                85              90              95

Gly Asn His Leu Cys Lys Ile Ala Ser Ala Ser Val Ser Phe Asn Leu
            100             105             110
```

| Tyr | Ala | Ser<br>115 | Val | Phe | Leu | Leu | Thr<br>120 | Cys | Leu | Ser | Ile | Asp<br>125 | Arg | Tyr | Leu |
|---|---|---|---|---|---|---|---|---|---|---|---|---|---|---|---|
| Ala | Ile<br>130 | Val | His | Pro | Met | Lys<br>135 | Ser | Arg | Leu | Arg | Thr<br>140 | Met | Leu | Val |
| Ala<br>145 | Lys | Val | Thr | Cys | Ile<br>150 | Ile | Ile | Trp | Leu | Met<br>155 | Ala | Gly | Leu | Ala | Ser<br>160 |
| Leu | Pro | Ala | Val | Ile<br>165 | His | Arg | Asn | Val | Tyr<br>170 | Phe | Ile | Glu | Asn | Thr<br>175 | Asn |
| Ile | Thr | Val | Cys<br>180 | Ala | Phe | His | Tyr | Glu<br>185 | Ser | Arg | Asn | Ser | Thr<br>190 | Leu | Pro |
| Ile | Gly | Leu<br>195 | Gly | Leu | Thr | Lys | Asn<br>200 | Ile | Leu | Gly | Phe<br>205 | Leu | Phe | Pro | Phe |
| Leu<br>210 | Ile | Ile | Leu | Thr | Ser<br>215 | Tyr | Thr | Leu | Ile | Trp<br>220 | Lys | Ala | Leu | Lys | Lys |
| Ala<br>225 | Tyr | Glu | Ile | Gln<br>230 | Lys | Asn | Lys | Pro | Arg<br>235 | Asn | Asp | Asp | Ile | Phe<br>240 | Arg |
| Ile | Ile | Met | Ala<br>245 | Ile | Val | Leu | Phe | Phe<br>250 | Phe | Phe | Ser | Trp | Val<br>255 | Pro | His |
| Gln | Ile | Phe | Thr<br>260 | Phe | Leu | Asp | Val | Leu<br>265 | Ile | Gln | Leu | Gly | Val<br>270 | Ile | His |
| Asp | Cys | Lys<br>275 | Ile | Ala | Asp | Ile | Val<br>280 | Asp | Thr | Ala | Met<br>285 | Pro | Ile | Thr | Ile |
| Cys | Ile<br>290 | Ala | Tyr | Phe | Asn | Asn<br>295 | Cys | Leu | Asn | Pro<br>300 | Leu | Phe | Tyr | Gly | Phe |
| Leu<br>305 | Gly | Lys | Lys | Phe | Lys<br>310 | Lys | Tyr | Phe | Leu | Gln<br>315 | Leu | Leu | Lys | Tyr | Ile<br>320 |
| Pro | Pro | Lys | Ala | Lys<br>325 | Ser | His | Ser | Ser | Leu<br>330 | Ser | Thr | Lys | Met | Ser<br>335 | Thr |
| Leu | Ser | Tyr | Arg<br>340 | Pro | Ser | Asp | Asn | Met<br>345 | Ser | Ser | Ala | Ala | Lys<br>350 | Lys | Pro |
| Ala | Ser | Cys<br>355 | Ser | Glu | Val | Glu | | | | | | | | | |

( 2 ) INFORMATION FOR SEQ ID NO:5:

( i ) SEQUENCE CHARACTERISTICS:
        ( A ) LENGTH: 2884 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

```
GGGGATGGAG  CGAGCACAGA  ATTGAAAGCT  TTCTTCAGCC  TGCATTTTAA  GGAGTGCGTG      60
TGGGAAGCTC  AGTAAGCTGA  TTTATGATAA  CTGCTTTAAA  CACTGGCAAC  TAAAAGAGTG     120
TAAGGATTGG  GAGTCTCTGA  CAGTTCAATA  TGAAGGACAA  CTTCAGTTTT  GCTGCCACCA     180
GCAGAAACAT  CACCAGCAGT  CTTCCTTTTG  ATAATCTCAA  CGCAACTGGC  ACCAATGAGT     240
CCGCATTTAA  CTGCTCACAC  AAACCGGCAG  ATAAGCATTT  GGAAGCAATT  CCTGTTCTCT     300
ACTACATGAT  TTTTGTGATT  GGTTTTGCTG  TTAACATTGT  TGTGGTCTCA  CTGTTTTGTT     360
GTCAAAAGGG  CCCTAAAAAG  GTGTCCAGCA  TTTACATCTT  CAATCTGGCT  GTGGCTGACT     420
TACTCCTTTT  GGCAACCCTT  CCTCTCTGGG  CAACCTATTA  CTCTTATAGA  TATGACTGGC     480
TCTTTGGACC  TGTGATGTGC  AAAGTGTTTG  GTTCTTTTCT  GACCCTGAAC  ATGTTTGCAA     540
GCATTTTTTT  TATTACGTGC  ATGAGTGTTG  ATAGGTACCA  ATCGGTTATC  TACCCTTTTC     600
```

| | | | | | |
|---|---|---|---|---|---|
| TGTCTCAGAG | AAGGAATCCC | TGGCAAGCAT | CTTATGTAGT | TCCCCTTGTT | TGGTGTATGG | 660 |
| CTTGTCTGTC | CTCATTGCCA | ACATTTTATT | TCCGAGATGT | CAGAACCATT | GAATACTTAG | 720 |
| GTGTGAATGC | TTGTATTATG | GCTTTCCCAC | CTGAGAAATA | TGCTCAGTGG | TCTGCTGGGA | 780 |
| TTGCCTTAAT | GAAAAATATT | CTTGGCTTTA | TCATTCCTTT | AATATTCATA | GCAACGTGTT | 840 |
| ACTTTGGAAT | CAGAAAACAT | CTGCTGAAGA | CCAATAGCTA | TGGGAAGAAC | AGAATTACCC | 900 |
| GTGACCAAGT | CTTGAAGATG | GCAGCTGCTG | TTGTGTTGGC | ATTCATCATT | TGCTGGCTTC | 960 |
| CCTTCCATGT | TCTGACCTTC | TTGGATGCTC | TGACCTGGAT | GGGTATCATT | AATAGCTGTG | 1020 |
| AAGTTATAGC | AGTCATTGAC | CTGGCACTTC | CTTTTGCCAT | CCTCCTGGGA | TTCACCAACA | 1080 |
| GCTGTGTTAA | TCCCTTCCTG | TATTGTTTCG | TTGGAAACCG | CTTCCAACAG | AAGCTCCGTA | 1140 |
| GTGTGTTTAG | AGTTCCCATT | ACTTGGCTCC | AAGGCAAGAG | AGAGACTATG | TCTTGCCGAA | 1200 |
| AAAGCAGTTC | TCTTAGAGAA | ATGGACACCT | TTGTGTCTTA | AATCTGTTAG | TGGGATGCAT | 1260 |
| GTAATCAGCC | TAGCAATGGT | TTGGAGGCCC | ACACAAATGA | TCTTTAAGTG | ACATCAGTAT | 1320 |
| AATATAATTC | TTTGCTTTTT | CTAATCTTTA | TTTACTCCCC | CCAGAACAGG | AAATAAGTAT | 1380 |
| AATTATAAAC | CTTTATACTC | CACCAGCTTT | CAGTGATAGT | GCCTTCTTTT | TCTGGTCCGT | 1440 |
| TGGCAGGAGA | TTGTCATATG | TGAGCTTTAT | CTATAATCTA | GAAGTATCTG | GGGGAATTAT | 1500 |
| CTCGACTTAT | AATTAAAAAC | AAATTATGAG | TGATGATTTG | ATGTCTCGGA | TTTCTCCCTG | 1560 |
| GAAAATGCTG | GCATTTCTTA | GTGGAGTTTT | ATGTCCATTT | TCATCTGATA | TTTTTTTCTC | 1620 |
| TTGAACAAGG | GCCAATTTGA | ACTTCTTACA | CTTTCCAACC | ATATGATAGA | GCATGAGAGG | 1680 |
| TGGGCACTAA | GGTTAGCATG | CTATACCCTT | CTATATATGC | CATAGGTTGG | TAGTGGCTTA | 1740 |
| TTCAGTCTCT | AAATATATAG | GTTCTCCTTT | TAAAGAAATT | ATAAGTTGTG | TTCCTTTTCC | 1800 |
| ATTTCACTCA | AGTATAGCTT | TTTACTTACT | ATCTAAAACC | ACTGAGTAGA | TCTAGAATGT | 1860 |
| GGTTAAATC | ACACTTCTCT | ATTAGCTTAT | CCTTGAAGTT | ATAGAGCGCA | CGCTATTTAG | 1920 |
| TAAAACAGAA | CTACCCTGAA | AAAGTATTTT | ATTAACCACA | AAACTGAATA | TACACTTGGA | 1980 |
| AAACTTTTCA | TCCATTTTGA | CTATTGTTTC | AAGTTTTCTA | TTCTCTTCTG | ATGATTTTTG | 2040 |
| AACACGACAA | CAAAACACTG | TATTATTAGA | TGACATAAAG | GTCACTTTTT | ACATTTTTAA | 2100 |
| CCTTTTGAAC | ATGGTGCTTT | GATATATTCT | ATGGTGACTT | GAGTTTAATT | ATTCATGCTT | 2160 |
| TTGTTCTGGG | CTGCGTCCCA | AAATATCTTT | TTGACCCTGA | AAAAGAGAGG | ATTCTTTAAT | 2220 |
| TCTTTAGCTT | TATAATAAAC | TGCACACTGG | CATAGGAAAA | GGTTATGTCA | GAATGGAAGT | 2280 |
| TTGATGCCTT | CTTGGGAGCA | AACAGACCCA | GAGAACGGC | AAGTTTGGTG | TCCAACAAGG | 2340 |
| AACTTGTCAG | AACAAAGGCC | CCTGGGGAGT | ATTTTGAATC | TGCATTTCTG | GGCACAGTTC | 2400 |
| CAGAATATAT | AAGAGTCTGT | GGAGGTGATT | TAAATCAAGC | CCAGGTCCAC | AGAGCTCATT | 2460 |
| CTCAACACGA | GTACATCTCT | TACATTAGAG | GAATATAATC | CCGGAAACTG | AGTCACCTAA | 2520 |
| AGTTCACTCA | AACTTCACAA | TAAGTATTAA | TTCAAACGTT | CAAAATGCCA | TTCTCTTACT | 2580 |
| GCCCCATATT | ATACCAGGTC | GCCTGAGACC | TTTCTGGACT | GATAATGACC | TCTGAGGTAG | 2640 |
| ATTTAAAGTT | TTGGGAACTT | AACATTTCTG | TCAGATTTCA | GGCTTTTTG | GTTGAAGAAT | 2700 |
| CCTCTCATAC | CCCTTCCTTG | GAAAACCCTG | ATTTCATGTA | TTCATATTAT | GTGTTACTAA | 2760 |
| GATCAAGTAG | CTAAATATAT | AATCAGTTAT | GATTTTGTGT | TTTAAGTAAT | TTACACAAC | 2820 |
| ATCTCATAAA | AATAAAATCA | TTATTGGGAA | AAAAAAAAAA | AAAAAAAAAA | AAAAAAAAA | 2880 |
| AAAA | | | | | | 2884 |

( 2 ) INFORMATION FOR SEQ ID NO:6:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Arg Lys His Leu Leu Lys Thr Asn Ser Tyr Gly Lys Asn Arg Ile Thr
1               5                   10                  15
Arg Asp Gln Val Leu Lys
            20
```

( 2 ) INFORMATION FOR SEQ ID NO:7:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Arg Met Val Ala Leu Lys Ala Gly Trp Gln Gln Arg Lys Arg Ser Glu
1               5                   10                  15
Arg Lys Ile Thr Leu
            20
```

( 2 ) INFORMATION FOR SEQ ID NO:8:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Arg Ile Tyr Ile Val Leu Arg Gln Arg Pro Leu Arg Glu Lys Lys Ala
1               5                   10                  15
Thr Gln
```

( 2 ) INFORMATION FOR SEQ ID NO:9:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Arg Ile Arg Thr Val Met Lys Thr Asp Gly Lys Arg Thr Asp Lys Leu
1               5                   10                  15
Glu Arg Leu Met Leu Arg
            20
```

( 2 ) INFORMATION FOR SEQ ID NO:10:

( i ) SEQUENCE CHARACTERISTICS:
        ( A ) LENGTH: 22 amino acids
        ( B ) TYPE: amino acid ( C ) STRANDEDNESS: single
            ( D ) TOPOLOGY: linear ( i i ) MOLECULE TYPE: peptide ( x i ) SEQUENCE DESCRIPTION: SEQ ID NO:10:

Arg  Ile  Arg  Thr  Ile  Met  Lys  His  Asp  Gly  Thr  Lys  Thr  Glu  Lys  Leu
1                   5                        10                       15

Glu  Lys  Leu  Met  Val  Arg
              20

( 2 ) INFORMATION FOR SEQ ID NO:11:

( i ) SEQUENCE CHARACTERISTICS:
            ( A ) LENGTH: 22 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:11:

Arg  Ile  Arg  Thr  Ile  Met  Lys  His  Asp  Gly  Thr  Lys  Thr  Glu  Lys  Leu
1                   5                        10                       15

Glu  Arg  Leu  Met  Val  Arg
              20

( 2 ) INFORMATION FOR SEQ ID NO:12:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:12:

ATTCCTGTTC TCTACTAC                                                            18

( 2 ) INFORMATION FOR SEQ ID NO:13:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:13:

GTAACACGTT GCTATGAA                                                            18

( 2 ) INFORMATION FOR SEQ ID NO:14:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:14:

CGGAACTGAA AGCTTACT                                                            18

( 2 ) INFORMATION FOR SEQ ID NO:15:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:15:

AAGGACAACT TCAGTTTT                                                    18

( 2 ) INFORMATION FOR SEQ ID NO:16:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:16:

AGACACAAAG GTGTCCAT                                                    18

CDNAS ENCODING MOUSE AND RAT TYPE-2 ANGIOTENSIN II RECEPTORS AND THEIR EXPRESSION IN HOST CELLS

The research carried out in the subject application was supported in part by grants from the National Institutes of Health. The government may have rights in any patent issuing on this application.

CROSS-REFERENCE TO RELATED APPLICATIONS

This application is a continuation-in-part of application Ser. No. 08/100,486, filed Jul. 30, 1993.

INTRODUCTION

1. Technical Field

The technical field of this invention concerns the identification and cloning of an angiotensin II type 2 receptor, a peptide hormone receptor involved in growth and differentiation, and the use of this novel receptor in the diagnosis and treatment of cardiovascular disease.

2. Background

Angiotensin II is an octapeptide hormone that induces a variety of physiological responses including vasoconstriction in cardiovascular tissues, reduced glomerular filtration rate in the kidneys, catecholamine and aldosterone secretion from adrenal gland, dipsogenia in the brain, and the induction of salt appetite and drinking behavior. Accordingly, there is a profound medical interest in regulating and exploiting host responsiveness to this molecule.

For over two decades, investigators have attempted to identify and characterize angiotensin II receptors. The physiological response diversity and studies with analogs of angiotensin II led researchers to speculate that multiple heterogeneous receptor types exist. Studies with nonpeptide angiotensin II receptor antagonists such as DuP 753 and PD 123177/123319 have classified receptor binding sites as type 1 ($AT_1$, which bind Dup 753) or type 2 ($AT_2$, which bind PD 123319). Recently, cDNAs encoding a rat and a bovine $AT_1$ receptor were reported.

The abundant expression of $AT_2$ receptors in fetal tissues, immature brain, skin wound and atretic ovarian follicles suggest a role in growth and development. Like $AT_1$ receptors, $AT_2$ receptors also appear to be involved in neointima formation after vascular injury. Unfortunately, the structure and character of the $AT_2$ receptors remain unknown. Also unknown are the clinical implications of therapeutic use of $AT_1$-specific antagonists on $AT_2$-mediated pathways, either directly or indirectly through altered serum angiotensin II levels. Thus, for both the development of new therapeutics and the optimization of existing treatments, especially relating to hypertension, there is an urgent need to define the $AT_2$ structure.

Using $AT_2$ receptor-specific antagonists, several studies have attempted to characterize $AT_2$ receptor structure and function. Despite these efforts and in part because of the receptor's instability and poor immunogenicity, $AT_2$ receptors have defied definitive identification, characterization and cloning. Without a source of recombinant $AT_2$ receptor, it has not been possible to assemble a defined assay to screen for modulators of $AT_2$ receptor-mediated growth/differentiation. Cloning and characterizing an $AT_2$ receptor would provide the pharmaceutical industry with the critical, missing ingredient for drug development relating to $AT_2$ receptor targeting, including cancer, cardiovascular disease, reproductive medicine, etc.; for refining existing therapeutic use of $AT_1$ receptor antagonists; and for developing specific cellular and model animal systems for the development of cardiovascular disease therapy.

Relevant Literature

For background on the angiotensin II receptors, see: Whitebread, S., Mele, M., Kamber, B. & de Gasparo, M. *Biochem. biophys. Res. Commun.* 163, 284–291 (1989); Chiu, A. T. et al. *Biochem. biophys. Res. Commun.* 165, 196–203 (1989); Millan, M. A. et al. *Science* 244, 1340–1342 (1989); Tsutsumi, K., Stromberg, C., Viswanathan, M. & Saavedra, J. M. *Endocrinology* 129, 1075–1082 (1991); Millan, M. A., Jacobowitz, D. M., Aguilera, G. & Catt, K. J. *Proc. natn. Acad. Sci. U.S.A.* 88, 11440–11444 (1991); Pucell, A. G., Hodges, J. C., Sen, I., Bumpus, F. M. & Husain, A. *Endocrinology* 128, 1947–1959 (1991); Dudley, D. T., Hubbell, S. E. & Summerfelt, R. M. *Mol. Pharmacol.* 40, 360–367 (1991); Yamano, Y., Ohyama, K., Chaki, S., Guo, D. F. & Inagami, T. *Biochem. biophys. Res. Commun.* 187, 1426–1431 (1992); Ohyama, K., Yamano, Y., Chaki, S., Kondo, T. & Inagami, T. *Biochem. biophys. Res. Commun.* 189, 677–683 (1992); Janiak, Pillon, Prost and Vilaine *Hypertension* 20, 737–745 (1992).

For the cloning of the type 1 receptor, see, Sasaki, K. et al. *Nature* 351, 230–233 (1991); Sasamura, H., Hein, L., Krieger, J. E., Pratt, R. E., Kobilka, B. K. & Dzau, V. J. *Biochem. biophys. Res. Commun.* 185, 253–259 (1992); Murphy, T. J., Alexander, R. W., Griendling K. K., Runge, M. S. & Bernstein, K. E. *Nature* 351, 233–236 (1991); Iwai, N. & Inagami, T. *FEBS Lett.* 298, 257–260 (1992).

For a description of other related proteins, see: Yamada, Y. et al. *Proc. natn. Acad. Sci. U.S.A.* 89, 251–255 (1992); Rens-Domiano, S. et al. *Mol. Pharmacol.* 42, 28–34 (1992); Sokoloff, P., Giros, B., Martres, M. P., Bouthenet, M. L. & Schwartz, J. C. *Nature* 347, 146–151 (1990); McEachern, A. E. et al. *Proc. natn. Acad. Sci. U.S.A.* 88, 7724–7728 (1991); Sreedharan, S. P., Robichon, A., Peterson, K. E. & Goetzl, E. J. *Proc. natn. Acad. Sci. U.S.A.* 88, 4986–4990 (1991); O'Dowd, B. F., Lefkowitz, R. J. & Caron, M. G. A. Rev. *Neurosci.* 12, 67–83 (1989); Gressens, P., Hill, J. M., Gozes, I., Fridkin, M. & Brenneman, D. E. *Nature* 362, 155–158 (1993).

SUMMARY OF THE INVENTION

Angiotensin II type 2 receptors ($AT_2$ receptor), structurally related cell receptors, nucleic acids encoding such $AT_2$ receptors, $AT_2$ receptor-related peptides, and methods of using $AT_2$ receptors and $AT_2$ receptor-encoding nucleic acids are provided. In particular, the present invention provides for the cloning of a class of unique seven-transmembrane receptors fulfilling the criteria of $AT_2$ receptors. $AT_2$ receptor-specific binding compounds are disclosed including antibodies to $AT_2$ receptor epitopes. The invention provides $AT_2$ receptor-based pharmaceutical compositions and $AT_2$ receptor-based methods for screening chemical libraries for regulators of cell growth/differentiation. In particular, the invention provides methods for identifying agonists and antagonists of the disclosed $AT_2$ receptors. Such compositions find broad utility in the treatment of cardiovascular disease, cancer, reproductive disease, etc. Additionally, the invention provides specific cellular and animal systems for the development of cardiovascular disease therapy.

BRIEF DESCRIPTION OF THE FIGURES

FIG. 1. Nucleotide (SEQ ID NO:01) and deduced amino acid (SEQ ID NO:02) sequences of the mouse $AT_2$ receptor cDNA. Putative transmembrane domains I–VII are indicated above the sequence. (*), potential N-glycosylation sites; (#), potential phosphorylation sites; two possible polyadenylation signals are underlined.

FIG. 2A, Saturation isotherm of the specific binding of [$^{125}$I] CGP42112A to membranes from COS-7 cells expressing the mouse $AT_2$ receptor. Inset shows a Scatchard plot of the same data. The estimated maximal binding, $B_{max}$, and $K_d$ values were 0.58 pmol per mg protein and 0.12 nM, respectively. FIG. 2B, Displacement of specific [$^{125}$I]CGP42112A binding in the mouse $AT_2$ receptor cDNA-transfected COS-7 cell membranes by unlabeled CGP42112A (●), [Sar$^1$, Ile$^8$]-Ang II (○), Ang II (▲), Ang I (□), PD123319 (■) and DuP753 (x).

FIG. 3. Comparison of the amino acid sequences between the mouse $AT_2$, rat $AT_2$ and mouse $AT_{1a}$ receptors. The amino acid sequences of the mouse $AT_2$ receptor (MOUSE $AT_2R$) (SEQ ID NO:02) rat $AT_2$ receptor (RAT $AT_2R$) (SEQ ID NO:03) and mouse $AT_{1a}$ receptor (MOUSE $AT_{1a}R$) are shown. Amino acids are represented by their single letter code. The putative transmembrane domains are indicated with a line. Amino acids in the rat $AT_2$ and mouse $AT_1$ sequences which are different from the corresponding mouse $AT_2$ sequences are reported. Gaps are inserted for maximum alignment.

FIG. 4A, Poly(A)$^+$ RNA (5 ug per lane), isolated from the heart (Ht), whole brain (Br), liver (Li) and whole fetus at 16–18 days of gestation (Fet), was electrophoresed and hybridized with a probe for the $AT_2$ receptor, or GAPDH as a control. FIG. 4B, Poly(A)$^+$ RNA from the same tissues above was analyzed by RT-PCR using the primers 1 and 2, as described in Materials and Methods.

FIG. 5A, Samples of mouse genomic DNA (10 ug) digested with restriction endonucleases EcoRI or BamHI were electrophoresed, blotted and hybridized with $^{32}$P-labeled mouse $AT_2$ receptor cDNA probe. FIG. 5B, Mouse $AT_2$ receptor cDNA clone (MC5) (lane 1) and mouse genomic DNA (lane 2) were analyzed by PCR using the primers 3 and 5 (upper), or the primers 4 and 5 (lower), as described in Materials and Methods. Both DNA samples yielded PCR products of the same size in either reaction. The left lane shows a DNA size marker PhiX174/HaeIII.

FIGS. 6A–6D. Restriction map (FIG. 6A) and nucleotide (SEQ ID NO:05) and deduced amino-acid sequence (SEQ ID NO:03) (FIG. 6B) of the rat $AT_2$ receptor clone pMRAT2. The open bar shows the coding region. Putative transmembrane domains I–VII are indicated above the sequence. (*), potential N-glycosylation sites; (#), potential phosphorylation sites; two possible polyadenylation signals are underlined; selective mRNA destabilizing signals are indicated by boxes. FIG. 6C, Sequence comparison between rat $AT_2$ (SEQ ID NP:03) and $AT_1$ (SEQ ID NO: 4) Boxes, identical amino-acid residues; bars, conservative substitutions. 6 conserved cysteine residues are outlined. Bold letters show consensus residues in the G protein-coupled receptor superfamily. FIG. 6D, Comparison in the third intracellular loop of rat $AT_2$, (SEQ ID NO:06), mouse SSTR1 (SEQ ID NO:07) and rat $D_3$ (SEQ ID NO:08) receptors (148 amino acids are not shown), and of the Drosophila cell polarity gene product Fz (SEQ ID NO:09) and two rat homologues, Fz-1 (SEQ ID NO:10) and Fz-2. SEQ ID NO: 11) Boxes indicate conserved residues.

DESCRIPTION OF SPECIFIC EMBODIMENTS

Figure 2A:
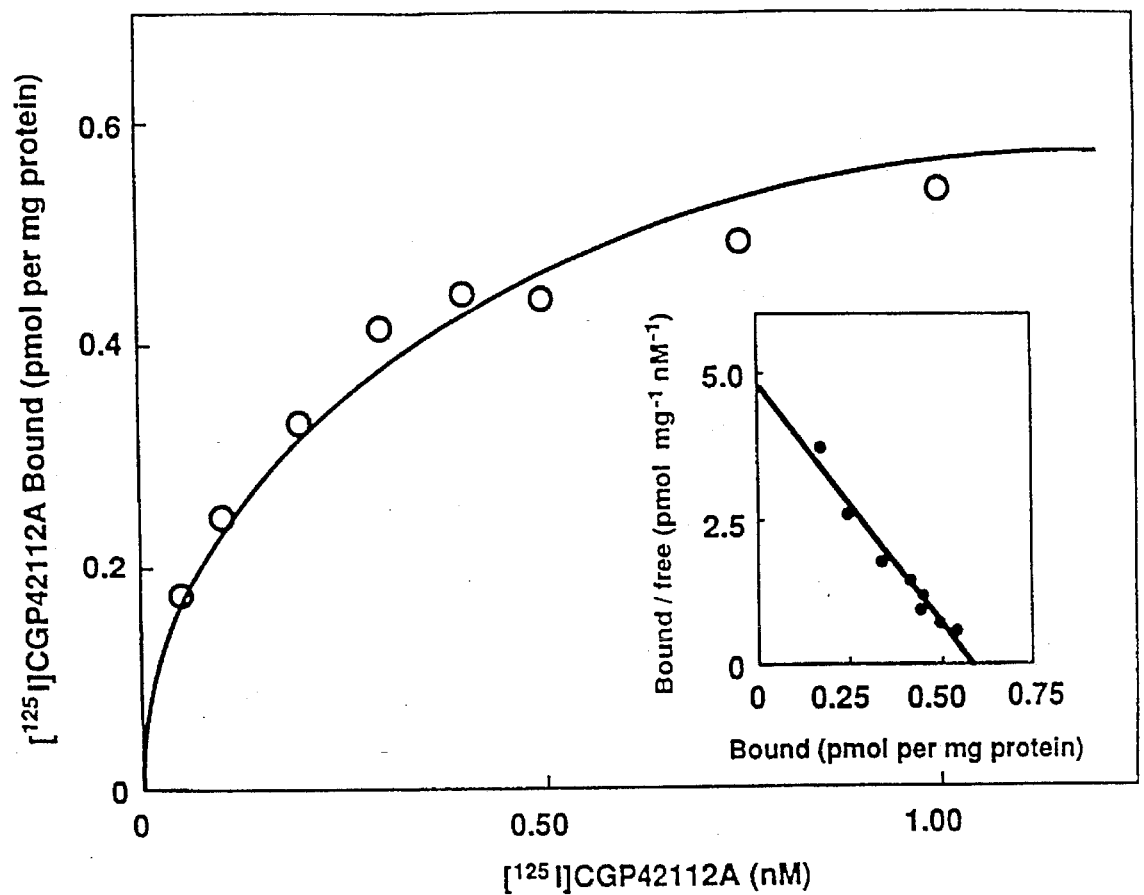
FIG. 2A and 2B. Binding characteristics of [$^{125}$I] CGP42112A to membranes prepared from COS-7 cells transfected with the mouse $AT_2$ receptor cDNA.

The present invention discloses a class of unique seven-transmembrane receptors fulfilling the criteria of $AT_2$ receptors: 1) ligand binding specificity, 2) effect of dithiothreitol (DTT) on binding characteristics, 3) lack of effect of guanylnucleotide analogues, 4) lack of phosphoinositide or calcium signalling, and 5) tissue distribution and developmental pattern of expression. In one embodiment, the invention provides isolated portions of the receptors, the $AT_2$ genes, and transcripts thereof.

As used herein, a "unique" portion of the disclosed $AT_2$ receptors or a $AT_2$ peptide is a peptide with a sequence unique to that disclosed in that it is not found in any previously known proteins. Thus a unique portion has an amino acid sequence length at least long enough to define a novel polypeptide. An $AT_2$ receptor portion is an at least about five, preferably at least about ten, more preferably at least about twenty amino acid sequence of the disclosed $AT_2$ receptor. Unique portions of the disclosed $AT_2$ receptor are readily identified by comparing the disclosed sequence with known protein sequence data bases. Particularly preferred unique portions are disclosed herein.

The disclosed full length $AT_2$ receptor sequences are about 363 amino acids. A substantially full-length sequence comprises or encodes at least about 240, preferably at least about 300, more preferably at least about 340 amino acids of the disclosed $AT_2$ receptor sequence; and typically includes at least 3, preferably about seven of the disclosed $AT_2$ receptor transmembrane regions.

An "angiotensin II type-2 binding specificity" means the subject polypeptide retains a molecular conformation specific to one of the disclosed $AT_2$ receptors that is specifically recognizable by a ligand, agonist, antibody, etc. of the $AT_2$ receptor. As such, $AT_2$ receptor binding specificities include $AT_2$ receptor-specific catalytic and signal transducing activity, immunological epitopes, lectin binding sites, and preferably $AT_2$ angiotensin II, agonist or antagonist binding sites.

"Specific binding" or recognition is empirically determined by contacting, for example the disclosed $AT_2$ receptor, with a mixture of components and identifying those components that preferentially bind the receptor. Specific binding is most conveniently shown by displacement of labeled ligand using recombinant $AT_2$ receptor cellular expression systems disclosed herein. Alternatively, solubilized, e.g. truncated or detergent treated, receptor may be used. Generally, specific binding of the subject $AT_2$ receptor has binding affinity of $10^{-6}$M, preferably $10^{-8}$M, more preferably $10^{-10}$M, under optimized in vitro conditions or conditions as exemplified below.

"Xenogeneic" $AT_2$ receptor analogs are nonhuman-derived proteins with substantial sequence identity to the disclosed $AT_2$ receptor. Nonhuman sources of $AT_2$ receptors analogs include animal sources, such as *Drosophila, Spodoptera*, and preferably mammalian sources. Of particular interest are rodents, primates, and livestock animals including bovine, ovine, equine and avian species "Substantial sequence similarity" means at least about 80%, more preferably at least about 90%, and most preferably at least about 95% sequence identity. Where substantially similar sequences diverge, the differences are preferably conservative, i.e. an acidic for an acidic amino acid substitution, a hydrophobic for a hydrophobic amino acid. Dissimilar sequences are typically aggregated within regions, especially within regions identified herein as transmembrane regions, rather than being distributed evenly over the polymer, and conserved (identical) sequences are typically aggregated within regions identified herein as other than transmembrane regions. An "isolated" peptide or polypeptide (poly/peptide) is unaccompanied by at least some of the material with which it is associated in its natural state. Generally, an isolated poly/peptide constitutes at least about 1%, preferably at least about 10%, and more preferably at least about 50% by weight of the total peptide and protein in a given sample. Included in the poly/peptide weight are alternative forms such as differentially glycosylated or phosphorylated or otherwise post-translationally modified forms. A stained band of the polypeptide is readily identified by Coomassie staining when the polypeptide, in isolated form, is subjected to electrophoresis according to the method of Laemmli, U. K. (1970) Nature 227, 680–685.

A composition comprising substantially pure poly/peptide is at least about 10%, preferably at least about 30%, more preferably at least about 70% by weight total peptide and protein. By pure polypeptide is intended at least about 90%, preferably at least 95%, and more preferably at least about 99% by weight of protein. Protein/peptide weight percentages are determined by dividing the weight of $AT_2$ receptor or fragments thereof, including alternative forms and analogs such as alternatively spliced, differentially phosphorylated or glycosylated, or otherwise post-translationally modified $AT_2$ receptors, present in a fraction by the total protein/peptide weight present.

The invention provides polypeptides containing unique peptides (and sequence homologs) of the disclosed $AT_2$ receptor having an $AT_2$-specific binding property. $AT_2$ receptor peptides find use in defining functional domains of $AT_2$ receptors, identifying compounds that associate with $AT_2$ receptors, designing compounds capable of modifying $AT_2$-receptor mediated cell signalling, for example, by binding or modulating an epitope or exploiting structural features of $AT_2$ receptors to directly modify signal transmission or transduction, as immunogens, and the like. Therapeutic $AT_2$ peptides are provided that are capable of interfering with $AT_2$ receptor-ligand binding or $AT_2$ receptor-mediated signal transmission or transduction. Typically, such peptides are effective by competitively inhibiting $AT_2$ receptor association with another compound, typically an $AT_2$ receptor ligand/agonist. Preferred peptides are selected for binding angiotensin, agonist or antagonist binding affinity using an $AT_2$ receptor cellular expression system such as disclosed herein. Particularly useful peptides include the ligand binding site (e.g. including lysine at position 183 such as peptide 164–184 and peptide 182–202), regions involved in ligand selectivity (e.g. surrounding His273) regions of low hydrophobicity (e.g. N- or C-terminal peptides and peptides spanning the regions between the transmembrane domains), and regions of low homology to $AT_1$ (e.g. peptide 103–120 and 219–239), including fragments thereof.

Other binding and associational domains of $AT_2$ receptors are ascertainable by those skilled in the art using the methods and compositions disclosed herein. For example, $AT_2$ receptor routants, including deletion mutants are generated from the disclosed $AT_2$ receptor sequence and used to identify regions important for specific protein-ligand or protein-protein interactions, for example, by assaying for the ability to mediate $AT_2$ signal transmission/transduction. Further, x-ray crystallographic data of the disclosed protein are used to rationally design binding molecules of determined structure or complementarity.

Selected peptides, preferably derived from recombinant products, are also readily modified through physical, chemical, and molecular techniques disclosed or cited herein or otherwise known to those skilled in the relevant art. For example, site directed mutagenesis of nucleotides in the DNA encoding the disclosed $AT_2$ receptor or for portions less than about 60 amino acids, in vitro peptide synthesis. Typically, amino acid insertions of about 1 to 10 amino acids, substitutions of single residues, and deletions of about 1 to 60 amino acids are made. Generally, mutatations of the disclosed $AT_2$ receptors are located in the non-transmembrane regions. Preferred mutations include:

| Deletions: | Insertions: | Substitutions: |
|---|---|---|
| Lys215 | 215-Glu—Ser—Ala | Lys215:Arg |
| Asp141—Tyr143 | | Asp90: Glu |
| (G-protein coupling | | Arg235—Lys256: |
| region) | | Trp219—Arg240 |
| Arg235—Lys240 | | His273:Xxx |
| Asp90 | | |

The subject peptides are subject to post-translational/sythesis modification to further modulate binding specificity/affinity by for examples, selection of the appropriate expression host, chemical/enzymatic intervention, etc. In particular, many of the disclosed $AT_2$ receptor peptides sequence contain serine and threonine residues which are phosphorylated or dephosphorylated. Preferred targets for phosphorylation are serine 348, 351, 352, 353 and threonine 346. See e.g. methods disclosed in Roberts et al. (1991) Science 253, 1022–1026 and in Wegner et al. (1992) Science 256, 370–373. Many of the disclosed $AT_2$ receptor peptides also contain glycosylation patterns which may modified, e.g. by enzymes like glycosidases or used to purify/identify the receptor, e.g. with lectins. Thus, mutagenesis is used to eliminate the N or O-linked glycosylation sites of the disclosed $AT_2$ receptor, e.g. Asn residues at 156, 242, 247, 314, 323 are sequentially deleted or substituted for by another basic amino acid such as Lys or His for N-linked glycosylation alterations, or deletions or polar substitutions are introduced at the forementioned Ser and Thr residues for modulating O-linked glycosylation. Glycosylation variants are also produced by selecting appropriate host cells, e.g. yeast, insect, or various mammalian cells, or by in vitro methods such as neuraminidase digestion. Useful expression systems include COS-7, 293, BHK, CHO, TM4, CV1, VERO-76, HELA, MDCK, BRL 3A, W138, Hep G2, MMT 060562, TRI cells, for examples. Other covalent modifications of the disclosed $AT_2$ receptor may be introduced by reacting the targeted amino acid residues with an organic derivatizing (e.g. methyl-3-[(p-azidophenyl)dithio]propioimidate) or crosslinking agent (e.g. 1,1-bis(diazoacetyl)-2-phenylethane) capable of reacting with selected side chains or termini. For therapeutic and diagnostic localization, the receptor and peptides thereof may be labeled directly (radioisotopes, fluorescers, etc.) or indirectly with an agent capable of providing a detectable signal, for example, a heart muscle kinase labeling site. Especially useful modifications (e.g. fatty acid-acylation, proteolysis, and site-directed mutations) alter receptor solubility, membrane transportability, stability, binding specificity and affinity, and signal transduction capability.

Compounds that specifically bind a portion of the disclosed $AT_2$ receptor are obtained using immunologic, chromatographic or synthetic methods available to those skilled in the art. Such compounds include specifically binding oligopeptides or oligonucleotides and specific antibodies that can be modified to a monovalent form, such as Fab, Fab', or Fv, and most preferably, small molecular weight organic angiotensin II agonists and antagonists. Anti-idiotypic antibody, especially internal imaging anti-iris are also prepared using the disclosures herein. Exemplary methods for producing $AT_2$ receptor-specific polyclonal or monoclonal antibodies are disclosed in Harlow and Lane, Antibodies, A Laboratory Manual, Cold Spring Harbor Laboratory, 1988.

$AT_2$-specific compounds find a wide variety of uses including therapeutic intervention in disease; for instance, $AT_2$ receptor-associated proteins are isolated by affinity immobilization or immunoprecipitation of $AT_2$ receptor complexes from cell lysates or membrane fractions. $AT_2$ receptor-derived peptides can be synthesized in pure form and also find use in diagnosis and therapy, for example, to modulate native $AT_2$ receptor interaction with native ligand. The oligopeptides will generally be more than six and fewer than about 60 amino acids, more usually fewer than about 30 amino acids, although large oligopeptides may be employed. A portion of the $AT_2$ receptor may be used in purified form, generally greater than about 90%, usually greater than about 95% pure. Methods for purifying such peptides to such purities include various forms of chromatographic, chemical, and electrophoretic separations disclosed herein or otherwise known to those skilled in the art.

The invention provides isolated nucleic acid sequences encoding an $AT_2$ receptor or unique portion thereof, including sequences substantially identical or homologous to sequences encoding such a receptor or epitope thereof. An "isolated" nucleic acid sequence is present as other than a naturally occurring chromosome or transcript in its natural state and typically is removed from at least some of the nucleotide sequences with which it is normally associated with on a natural chromosome. A complementary sequence hybridizes to a unique portion of the disclosed $AT_2$ receptor sequence under low stringency conditions, for example, at 50° C. and SSC (0.9M saline/0.09M sodium citrate) and that remains bound when subject to washing at 55° C. with SSC. Regions of non-identity of complementary nucleic acids are preferably or in the case of homologous nucleic acids, a nucleotide change providing a redundant codon. A partially pure nucleotide sequence constitutes at least about 5%, preferably at least about 30%, and more preferably at least about 90% by weight of total nucleic acid present in a given fraction.

Unique portions of the disclosed nucleic acid sequence are of length sufficient to distinguish previously known nucleic acid sequences. Thus, a unique portion has a nucleotide sequence at least long enough to define a novel oligonucleotide. Preferred nucleic acid portions encode a unique $AT_2$ receptor peptide. The nucleic acids of the invention and portions thereof, other than those used as PCR primers, are usually at least about 60 bp and usually less than about 6 kb in length. PCR primers are generally between about 15 and 100 nucleotides in length.

Figure 1A:
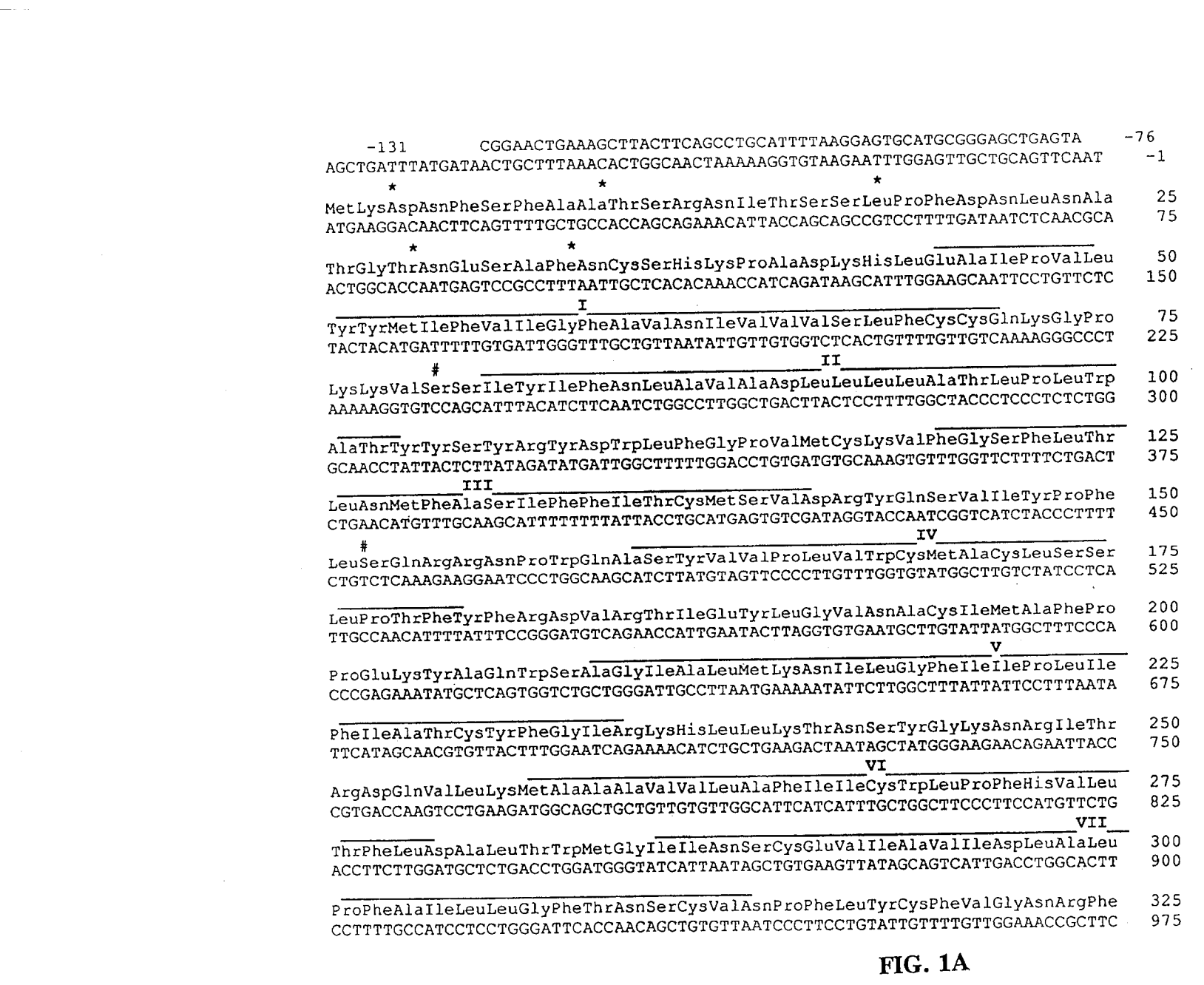

The nucleotide (cDNA) sequence encoding a full length $AT_2$ receptor is disclosed in FIG. 1. (SEQ ID NO:11) The disclosure also provides for the disclosed sequence modified by transitions, transversions, deletions, insertions, or other modifications such as alternative splicing and also provides for genomic $AT_2$ receptor sequences, and gene flanking sequences, including regulatory sequences; included are DNA and RNA sequences, sense and antisense. Preferred DNA sequence portions include portions encoding the preferred amino acid sequence portions disclosed above, portions between about 6 and about 36 amino acids including Lys215, or Asp90, the peptide Asp141-Try143 or the peptide Arg235-Lys240. For antisense applications where the inhibition of $AT_2$ receptor expression is indicated, especially useful oligonucleotides are between about 10 and 30 nucleotides in length and include sequences surrounding the disclosed ATG start site, especially the oligonucleotides defined by the disclosed sequence beginning about 5 nucleotides before the start site and ending about 10 nucleotides after the disclosed start site. Other especially useful $AT_2$ receptor mutants involve deletion or substitution modifications of the disclosed cytoplasmic C-terminus. Accordingly, $AT_2$ receptor mutants with angiotensin II binding affinities but with altered intracellular signal transductions capacities are produced. Preferred C-terminus deletion routants with impair transduction ability include $AT_2$ receptor with deleted amino acids 314–363 or 326–363.

For modified $AT_2$ receptor-encoding sequences or related sequences encoding proteins with $AT_2$ receptor-like functions, there will generally be substantial sequence identity between at least a segment thereof and a segment encoding at least a portion of the disclosed $AT_2$ receptor sequence, preferably at least about 60%, more preferably at least 80%, most preferably at least 90% identity. Homologous segments are particularly within regulatory regions and regions encoding protein domains involved in protein-protein or protein-ligand interactions, particularly $AT_2$ receptor-angiotensin II interactions and differences within such segments are particularly conservative substitutions.

Typically, the invention's $AT_2$ receptor encoding polynucleotides are associated with heterologous sequences. Examples of such heterologous sequences include regulatory sequences such as promoters, enhancers, response elements, signal sequences, polyadenylation sequences, etc., introns, 5' and 3' noncoding regions, etc. Other useful heterologous sequences are known to those skilled in the art or otherwise disclosed in references cited herein. According to a particular embodiment of the invention, portions of the $AT_2$ receptors encoding sequence are spliced with heterologous sequences to produce fusion proteins. For example, most of the $AT_2$ receptor peptides are expressed as soluble, secreted fusion proteins using appropriate signal sequences and optionally, a fusion partner such as β-Gal.

The disclosed sequences are also used to identify and isolate natural $AT_2$ receptors analogs, including xenogeneic analogs. Further, as the present disclosure documents a unique class of seven-transmembrane receptors for which G protein coupling has not been demonstrated, the disclosed compositions and methods are used to identify, characterize, isolate, and purify other members of this class. In particular, the disclosed nucleic acid sequences are used as hybridization probes under low-stringency or PCR primers, e.g. oligonucleotides encoding functional $AT_2$ receptor domains are $^{32}$P-labeled and used to screen λcDNA libraries at low stringency to identify similar cDNAs that encode proteins with related functional domains. Additionally, nucleic acids encoding at least a portion of the disclosed $AT_2$ receptor are used to characterize tissue specific expression of $AT_2$ receptor as well as changes of expression over time, particularly during organismal development or cellular differentiation.

The $AT_2$receptor encoding nucleic acids can be subject to alternative purification, synthesis, modification, sequencing, expression, transfection, administration or other use by methods disclosed in standard manuals such as Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, New York, N.Y., 1992) or that are otherwise known in the art. For example, the nucleic acids can be modified to alter stability, solubility, binding affinity and specificity, etc. $AT_2$ receptor-encoding sequences can be selectively methylated, etc. The nucleic acid sequences of the present invention may also be modified with a label capable of providing a detectable signal, either directly or indirectly. Exemplary labels include radioisotopes, fluorescers, biotinylation, etc. The invention also provides vectors comprising nucleic acids encoding $AT_2$ receptor or analogs. A large number of vectors, including plasmid and viral vectors, have been described for expression in a variety of eukaryotic and prokaryotic hosts. Advantageously, vectors may also include a promotor operably linked to the $AT_2$ receptor-encoding portion. Vectors will often include one or more replication systems for cloning or expression, one or more markers for selection in the host, e.g. antibiotic resistance, and one or more expression cassettes. The inserted $AT_2$ receptor coding sequences may be synthesized, isolated from natural sources, prepared as hybrids, etc. Suitable host cells may be transformed/transfected/infected by any suitable method including electroporation, $CaCl_2$ mediated DNA uptake, viral infection, microinjection, microprojectile, or other methods.

Appropriate host cells include bacteria, archebacteria, fungi, especially yeast, and plant and animal cells, especially mammalian cells. Of particular interest are *E. coli, B. subtilis, Saccharomyces cerevisiae*, SF9 cells, C129 cells, 293 cells, Neurospora, and CHO, COS, HeLa cells, immortalized mammalian myeloid and lymphoid cell lines, and pluripotent cells, especially mammalian ES cells and zygotes. Preferred replication systems include M13, ColE1, SV40, baculovirus, lambda, adenovirus, AAV, BPV, etc. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced $AT_2$ receptor or analogs.

For the production of stably transformed cells and transgenic animals, nucleic acids encoding the disclosed $AT_2$ receptor may be integrated into a host genome by recombination events. For example, such a sequence can be microinjected into a cell, and thereby effect homologous recombination at the site of an endogenous gene, an analog or pseudogene thereof, or a sequence with substantial identity to an $AT_2$ receptor-encoding gene. Other recombination-based methods such as nonhomologous recombinations, deletion of endogenous gene by homologous recombination, especially in pluripotent cells, etc., provide additional applications. Preferred transgenics and stable transformants overexpress the disclosed receptor gene and find use in drug development and as a disease model. Alternatively, knock-out cells and animals find use in development and functional studies. Methods for making transgenic animals, usually rodents, from ES cells or zygotes are known to those skilled in the art.

The compositions and methods disclosed herein may be used to effect gene therapy. See, e.g. Zhu et al. (1993) Science 261, 209–211; Gutierrez et al. (1992) Lancet 339, 715–721. For example, cells are transfected with $AT_2$ receptor sequences operably linked to gene regulatory sequences capable of effecting altered $AT_2$ receptor expression or regulation. To modulate $AT_2$ receptor translation, cells may be transfected with complementary antisense polynucleotides.

For gene therapy involving the transfusion of $AT_2$ receptor transfected cells, administration will depend on a number of variables that are ascertained empirically. For example, the number of cells will vary depending on the stability of the transfused cells. Transfusions media is typically a buffered saline solution or other pharmacologically acceptable solution. Similarly the amount of other administered compositions, e.g. transfected nucleic acid, protein, etc., will depend on the manner of administration, purpose of the therapy, and the like.

The invention provides methods and compositions for identifying agents useful in modulating host angiotensin II responsiveness. Such agents find use in the diagnosis or treatment of disease, particularly cardiovascular disease and cancer.

Typically, prospective agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means.

Useful agents are identified with a range of assays employing an $AT_2$ receptor or encoding nucleic acids. Particularly, cells transfected with $AT_2$ receptor-encoding DNA is used in in vitro binding assays with prospective agonists/antagonists/ligands. For instance, the effect of prospective agents on $AT_2$ receptor-angiotensin II binding may be assayed. Preferred transfects encode deletion routants, especially C-terminal deletion mutants, of the disclosed receptor sequence. Alternatively, the intracellular C-terminal domain is substituted with a sequence encoding a oligopeptide or polypeptide domain that provides an intracellular signal upon ligand binding different from the natural receptor. More preferably, such signal is more easily detected as a direct index of specific receptor-ligand binding to the host cell surface. Useful intracellular domains include those of the human insulin receptor and the TCR, especially domains with kinase activity and domains capable of triggering calcium influx which is conveniently detected by fluorimetry by preloading the host cells with Fura-2. Preferred assays are amenable to scaled-up, high throughput usage suitable for volume drug screening. Such screening will typically require the screening of at least about 10, preferably at least about 100, and more preferably at least about 1000 agents per week. A particular exemplary screen assays displacement of radiolabled CGP42112A from 293 cells stably transfected with $AT_2$ receptor-encoding nucleic acids.

Useful agents are typically those that bind to the $AT_2$ receptor or disrupt the association of $AT_2$ receptor with angiotensin II. Preferred agents are $AT_2$ receptor-specific and to not cross react with any $AT_1$ receptor nor affect $AT_1$ receptor-angiotensin II interactions. Useful agents may be found within numerous chemical classes, though typically they are organic compounds; preferably small organic compounds. Small organic compounds have a molecular weight of more than 100 yet less than about 4,500, preferably less than about 1500, more preferably, less than about 500. Exemplary classes include peptides, saccharides, steroids, heterocyclics, polycyclics, substituted aromatic compounds, and the like.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways to enhance their proteolytic stability, such as using an unnatural amino acid, such as a D-amino acid, particularly D-alanine, by functionalizing the amino or carboxyl terminus, e.g., for the amino group, acylation or alkylation, and for the carboxyl group, esterification or amidification, or the like. Other methods of stabilization may include encapsulation, for example, in liposomes, etc.

Agents may be prepared in a variety of ways known to those skilled in the art. For example, peptides under about 60 amino acids can be readily synthesized today using conventional commercially available automatic synthesizers. Alternatively, DNA sequences may be prepared encoding the desired peptide and inserted into an appropriate expression vector for expression in a prokaryotic or eukaryotic host. A wide variety of expression vectors are available today and may be used in conventional ways for transformation of a competent host for expression and isolation. If desired, the open reading frame encoding the desired peptide may be joined to a signal sequence for secretion, so as to permit isolation from the culture medium. Methods for preparing the desired sequence, inserting the sequence into an expression vector, transforming a competent host, and growing the host in culture for production of the product may be found in U.S. Pat. Nos. 4,710,473, 4,711,843 and 4,713,339.

For therapeutic uses, the compositions and agents disclosed herein may be administered by any convenient way, preferably parenterally, conveniently in a physiologically acceptable carrier, e.g., phosphate buffered saline, saline, deionized water, or the like. Typically, the compositions are added to a retained physiological fluid such as blood or synovial fluid. Generally, the amount administered will be empirically determined, typically in the range of about 10 to 1000 µg/kg of the recipient. For peptide agents, the concentration will generally be in the range of about 100 to 500 µg/ml in the dose administered. Other additives may be included, such as stabilizers, bactericides, etc. These additives will be present in conventional amounts.

The following examples are offered by way of illustration and not by way of limitation.

EXAMPLES

Example 1

Cloning and Analysis of rat $AT_2$ receptor.

cDNA prepared from size-fractionated (>1 kb) poly(A)$^+$ RNA (Sprague-Dawley whole rat fetus, 18 days postcoitum) was ligated into an expression vector pcDNAI (Invitrogen), and amplified in 900 pools of 1,000 clones. Plasmid DNA prepared from every 8 pools by the alkali lysis method was transfected over 2–3 h using DEAE-dextran/chloroquine into COS-7 cells grown on glass chamber slides (Nunc) (Mathews, L. S. & Vale, W. W. Cell 65, 973–982 (1991)). 48–60 h after transfection, cells were washed with 50 mM Tris-HCl, pH 7.4, containing 0.1% BSA and incubated with 200 pM $^{125}$I-[Sar$^1$,Ile$^8$]-Ang II (2,200 Ci umol$^1$, NEN) with or without 1 mM DuP753 for 2 h at room temperature. Cells were then washed four times with cold 50 mM Tris-HCl, pH 7.4, fixed with 0.1% glutaraldehyde at 4 C and subjected to emulsion autoradiography (Mathews, L. S. & Vale, W. W. Cell 65, 973–982 (1991)). As a positive control, the mouse $AT_{1b}$ receptor clone (Sasamura, H., Hein, L., Krieger, J. E., Pratt, R. E., Kobilka, B. K. & Dzau, V. J. Biochem. biophys. Res. Commun. 185, 253–259 (1992)) was transfected similarly, and constantly resulted in a positive staining over 20% of cells that was completely abolished by 1 uM DuP753. Positive pool (RF904) which gave 20 DuP753-resistant positive cells was divided into subpools and rescreened, and after three rounds of screening a single clone pMRAT2 was isolated. Sequencing of both strands of clone pMRAT2 was done by the dideoxy chain termination method with Sequenase (USB).

Radioligand binding to membranes from pMRAT2-transfected COS-7 cells indicates that the expressed protein has pharmacology indistinguishable from that of $AT_2$ receptor. Binding assays were performed with crude membranes isolated from COS-7 cells (Sasamura, H., Hein, L., Krieger, J. E., Pratt, R. E., Kobilka, B. K. & Dzau, V. J. Biochem. biophys. Res. Commun. 185, 253–259 (1992)) transiently transfected with pMRAT2. Reactions were performed in 100 ml of 20 mM Tris-HCl, pH 7.4, containing 0.25% BSA and 0.1 uM PMSF, $^{125}$I-CGP42112A (2,176 Ci mmol$^{-1}$, Peptide Radioiodination Center, Washington State Univ.), 5 ug membranes and various concentrations of unlabelled ligands. 2 h after incubation at room temperature, bound and free ligands were separated with GF/C filters (Whatman). 150 pM of radioligand was used for displacement experiments. Nonspecific binding was defined in the presence of 1 uM unlabelled CGP42112A and was 5% of total binding. Each experiment was carried out at least twice in duplicate, and the results shown here represent one experiment.

Single-component, saturable, high-affinity binding sites for an $AT_2$-selective ligand $^{125}$I-CGP42112A with a dissociation constant ($K_d$) of 0.17 nM were observed in pMRAT2-transfected cells but not untransfected cells or cells transfected with the vector DNA. Competition profiles yielded an order of inhibition potency of [Sar$^1$,Ile$^8$]-Ang II=CGP42112A≧Ang II>PD123319[10,15]>Ang I. DuP753, an $AT_1$-selective antagonist, has no effect. As with previous reports, DTT increased binding affinity for both Ang II and CGP42112A by 50–100%.

Figure 6A:
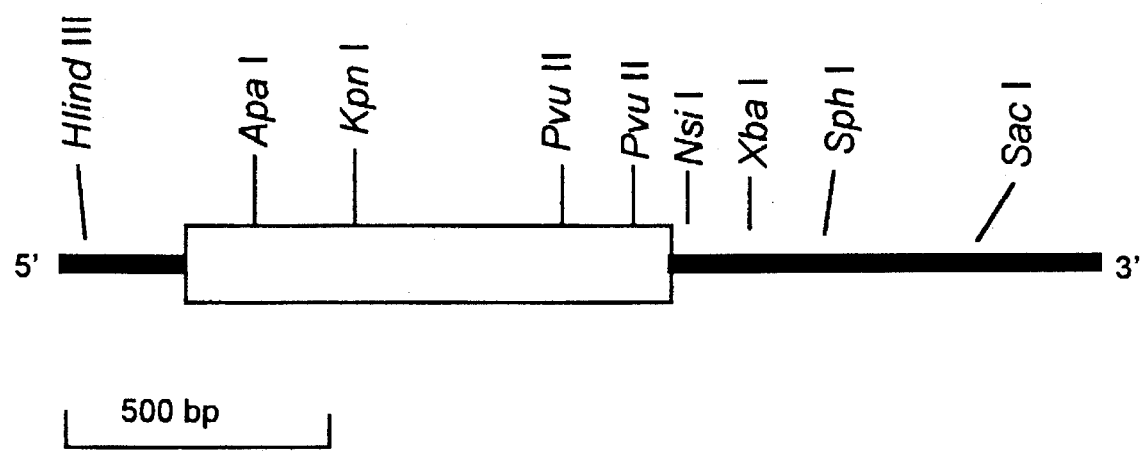

FIG. 6A reveals a 2,884-nucleotide cDNA (SEQ ID NO:05) encoding a deduced 363-amino-acid $AT_2$ receptor with a molecular mass of 41,330 attributable to its amino acid sequence. Hydropathy analysis indicates seven putative transmembrane domains. Two recently reported $AT_1$ receptor clones have the closest homology (34% identical and 53% similar amino acids), followed by receptors for somatostatin (both SSTR1 and SSTR2), bradykinin and vasoactive intestinal peptide (VIP)(30–32% sequence identity). There are 5 consensus N-glycosylation sites in the N-terminus, and several serine and threonine residues in the cytoplasmic domains—preferred phosphorylation sites.

$AT_2$ receptor has a transmembrane topology similar to $AT_1$ receptor with consensus residues found in other seven-transmembrane receptors. (SEQ ID NO:03) Similarity is highest in the second and fifth transmembrane domains with 2 stretches of 6-amino-acid identity that may be involved in ligand binding. Indeed, Lys-199 in the $AT_1$ receptor shown to be essential for Ang II binding is conserved. 6 cysteine residues are conserved. $AT_2$ receptor has 8 additional cysteine residues which may play a role in its binding characteristics in response to DTT.

Northern blot analysis of poly (A)$^+$ RNA from rat tissues revealed a 3.5-kb hybridizing band. For Northern blot analysis of mRNA from fetal rat tissues, poly(A)$^+$ RNA (5 ug per lane) was electrophoresed and RNA blot hybridization analysis was carried out as described in Naftilan, A. J., Pratt, R. E. & Dzau, V. J. *J. clin. Invest.* 83, 1419–1424 (1989) using the 2.4-kb HindIII-SacI fragment excised from clone pMRAT2 and the 0.78-kb PstI-XbaI fragment of a human glyceraldehyde-3-phosphate dehydrogenase (GAPDH) clone (ATCC), as probes. We found that the mRNA is abundant in whole fetus but decreases rapidly after birth. In adult, it is highly expressed in the adrenal, present in the brain and uterus but undetectable in the heart. This tissue distribution and the developmental regulation of the mRNA differ from $AT_1$ receptor mRNA but is identical with $AT_2$ receptor as reported by ligand binding.

In spite of structural similarity of this receptor with $AT_1$ and other 'classical' G protein-coupled receptors, its signal transduction mechanism is clearly unique. Unlike the cloned $AT_1$ receptor, when transiently expressed in COS-7 cells, stimulation of cloned $AT_2$ receptor failed to increase $IP_3$ or intracellular calcium. For the $IP_3$ study, COS-7 cells 48 h after transfection with either a control vector, an $AT_1$ receptor clone, or an $AT_2$ receptor clone were suspended in DMEM and stimulated with 1 uM Ang II for 15 sec at 37 C. Intracellular $IP_3$ levels were measured using radioreceptor assay (NEN). For calcium measurements, COS-7 cells on glass coverslips 48 h after transfection were incubated with 10 uM fura-2 AM (Molecular Probes) for 20 min at 37 C and stimulated with 1 uM Ang II. Cell fluorescence was measured with excitation at 340 nm and 380 nm. Ionomycin (10 uM) and EGTA (10 mM) were used for calibration.

We also examined cAMP and cGMP levels and phosphatase activity and saw no apparent effects. Furthermore, the ligand displacement curve of this receptor was not affected by guanylnucleotide analogues. These results are consistent with previous observations on the endogenously expressed $AT_2$ receptor, suggesting either the lack of G protein coupling or coupling to a unique G protein with a distinct signalling mechanism, or inefficient G protein coupling to the overexpressed receptor in COS-7 cells.

Mutagenesis demonstrated the importance of the third intracellular loop in G protein coupling of the $AT_1$ receptor. A comparison of the three intracellular loops in the $AT_1$ and $AT_2$ receptors reveals the lowest homology in this third loop. A comparison with the third loop of other receptors without demonstrable G protein coupling ($D_3$, SSTR1 and $AT_2$) reveals a conserved, 5-amino-acid motif (FIG. 1d). This motif is poorly conserved in $AT_1$ (1/5 identical), $D_1$ (2/5 identical) or SSTR2 receptor (0/5 identical). The present results indicate that $AT_2$, SSTR1 and $D_3$ receptors belong to a unique class of receptors, and that this motif is responsible for the apparent lack of tight coupling to 'classical' G proteins and may be involved in coupling to an as yet unidentified G protein(s), or may mediate an unknown signalling mechanism without G protein coupling. With regards to function, both SSTR1 and $AT_2$ receptors (plus an uncloned VIP receptor that is GTP-insensitive) are associated with development and growth. Moreover, these receptors ($AT_2$, SSTR1, $D_3$ and VIP) all exhibit fetal/neonatal and/or neuronal-specific expression.

The *Drosophila* frizzled protein, Fz, whose expression is developmentally regulated and is essential for normal epidermal morphogenesis and hair polarity (Vinson, C. R., Conover, S. & Adler, P. N. *Nature* 338, 263–264 (1989)), has a seven-transmembrane structure with a strikingly similar third loop to the $AT_2$ receptor including this motif (64% overall similarity in loop 3 to the $AT_2$ receptor; 3/5 identical, 5/5 similar in the motif) (FIG. 6d). Furthermore, its rat homologues (Fz-1 and Fz-2) have well conserved third loop and are highly expressed in neonatal tissues and in adult uterus, ovary, and brain (Chan, S. D. H. et al. *J. biol. Chem.* 267, 25202–25207 (1992)). The similar tissue distribution of the $AT_2$ receptor suggests a role similar to that of Fz in cell morphogenesis and related events in growth and development. Alternatively, these receptors might function as ligands for other unknown receptors. Indeed, another *Drosophila* seven-transmembrane protein with developmental cues, boss gene product (Kramer, H., Cagan, R. L. & Zipursky, L. *Nature* 352, 207–212 (1991)), acts as a ligand for sevenless tyrosine-kinase receptor during eye development.

Example 2

Murine $AT_2$ Receptor: Cloning and Functional Analysis.

Materials. Ang II, Ang I, and a non-selective Ang II receptor antagonist, [Sar$^1$,Ile$^8$]-Ang II, were purchased from Sigma (St. Louis, Mo.). An $AT_2$-selective ligand CGP42112A was a gift from Ciba-Geigy (Basel, Switzerland); [$^{125}$I]CGP42112A from Peptide Radioiodination Center (Washington State Univ., Washington). Another $AT_2$-selective ligand, PD 123319, was a gift from Parke-Davis (Ann Arbor, Mich.).

Molecular Cloning by Plaque Hybridization. Total RNA was prepared from 16–18-day whole Balb/c mouse fetus using RNAzol (Tel-Test, Friendswood, Tex.). Poly(A)$^+$ RNA was isolated using PolyATtract mRNA Isolation Systems (Promega, Madison, Wis.). A cDNA library carrying cDNAs larger than 2.0 kilobase pairs (kb) was prepared in lZAPII vector (Stratagene, La Jolla, Calif.). A HindIII/SacI fragment of rat $AT_2$ receptor cDNA was used as a probe (herein). Clones (4.3×10$^5$) derived from the cDNA library were transferred to nylon membranes (Colony/Plaque Screen Hybridization Transfer Membrane, Du Pont-NEN, Boston, Mass.) and screened by hybridization to rat $AT_2$ receptor cDNA. Hybridization was carried out at 42° C. in 2×SSC containing 5×Denhardt's solution, 1% SDS, 30% formamide, 10% dextran sulphate, 100 mg/ml heat-denatured salmon sperm DNA (Sigma) and the radiolabeled probe (10$^6$ cpm/ml) for 12 h. Filters were washed twice at 42° C. in 2×SSC containing 1% SDS for 40 min and in 0.2×SSC containing 1% SDS for 40 min. Eight positive clones were picked up and converted to plasmids via in vivo excision method and sequenced. One of the clones was revealed to be a full-length clone (MC5).

Expression in COS-7 Cells and Ligand Binding Assay. The EcoRI/XhoI insert of MC5 was subcloned into pcDNA I (Invitrogen, San Diego, Calif.), and the plasmid was transfected into COS-7 cells by modified DEAE-dextran method (Sussman, D. J., and Milman, G. (1984) Mol. Cell. Biol. 4, 1641–1643; and herein). The transfected cells were harvested and homogenized. The 100,000×g pellet of this homogenate was suspended and used as a membrane fraction. [$^{125}$I]CGP42112A binding in the membrane was determined as described herein. Displacement experiment was carried out with 0.2 nM [$^{125}$I]CGP42112A in the presence of various concentrations of compounds.

Northern Blot Analysis. Poly(A)$^+$ RNA from each tissue was separated by electrophoresis on a 1% agarose gel, and transferred onto a nylon membrane (GeneScreen, Du Pont-NEN). Hybridization was carried out as described previously (herein; Naftilan, A. J., Pratt, R. E., and Dzau, V. J. (1989) J. Clin. Invest. 83, 1419–1424) using a $^{32}$P-labeled HindIII-NsiI fragment excised from clone MC5. To assess equal loading of the lanes, the blots were similarly hybridized with a 0.78-kb PstIXbaI fragment of a human glyceraldehyde-3-phosphate dehydrogenase (GAPDH) clone (American Type Culture Collection, Rockville, Md.).

Genomic Southern Blot Analysis. Genomic DNA (10 ug) from Balb/c mouse liver (Clontech, Palo Alto, Calif.) was digested with restriction endonucleases EcoRI or BamHI, electrophoresed on a 1% agarose gel, and blotted to a nylon membrane (GeneScreen). The membrane was hybridized with the $^{32}$P-labeled full-length mouse AT$_2$ receptor cDNA probe (EcoRI/XhoI fragment excised from clone MC5). Hybridization was carried out at 42° C. in 5×SSPE containing 0.5% SDS, 50% formamide, 10% dextran sulphate, 100 mg/ml heat-denatured salmon sperm DNA and the radiolabeled probe (10$^6$ cpm/ml) for 24 h. The filter was washed twice at 56° C. in 0.2×SSC containing 0.1% SDS for 30 min.

Polymerase Chain Reaction (PCR). For reverse transcription-PCR (RT-PCR), first strand cDNA was synthesized from the mRNA using random primers and Molony Murine Leukemia Virus reverse transcriptase (GeneAmp PCR Reagent Kit, Perkin Elmer Cetus, Norwalk, Conn.). Mouse genomic DNA and mouse AT$_2$ receptor cDNA clone (MC5) were analyzed by PCR to examine the presence of introns in the coding region. PCR primers for AT$_2$ receptor are as follows: 5'-ATTCCTGTTCTCTACTAC- 3' (primer 1) (SEQ ID NO:12) 5'-GTAACACGTTGCTATGAA-3' (primer 2) (SEQ ID NO:13) 5'-CGGAACTGAAAGCTTACT-3' (primer 3) (SEQ ID NO:14) 5'-AAGGACAACT-TCAGTTTT-3' (primer 4) (SEQ ID NO:15), and 5'-AGA-CACAAAGGTGTCCAT-3' (primer 5) (SEQ ID NO:16) These primers are designed from mouse AT$_2$ receptor sequence and they are specific for the AT$_2$ receptor and quite different from the AT$_1$ receptor. PCR primers for mouse GAPDH were purchased from Clontech. Mouse liver DNA (Clontech) was used for the analysis of the gene encoding the AT$_2$ receptor. Reaction was carried out with 30 cycles of 1 min of denaturation at 94° C., 1 min of annealing at 50° C. and 3 min of extension at 72° C.

The nucleotide (SEQ ID NO:01) and deduced amino acid (SEQ ID NO:02) sequences of the mouse AT$_2$ receptor cDNA clone, MC5, are shown in FIG. 1. MC5 contains the 2.8-kb insert which has an open reading frame of 1089 base pairs. The deduced amino acid sequence consists of 363 amino acids with a relative molecular mass of 41373. Hydropathy analysis of the deduced amino acid sequence reveals putative seven transmembrane domains. There are 5 consensus sites for N-glycosylation (Hubbard, S. C., and Ivatt, R. J. (1981) Annu. Rev. Biochem. 50, 555–583) in a relatively long N-terminal extracelluar domain and 5 serine and 1 threonine residues in the cytoplasmic domains for possible phosphorylation (Kemp, B. E., and Person, R. B. (1990) Trends Biochem. Sci. 15, 342–346) identical to the rat AT$_2$ receptor.

Figure 2B:
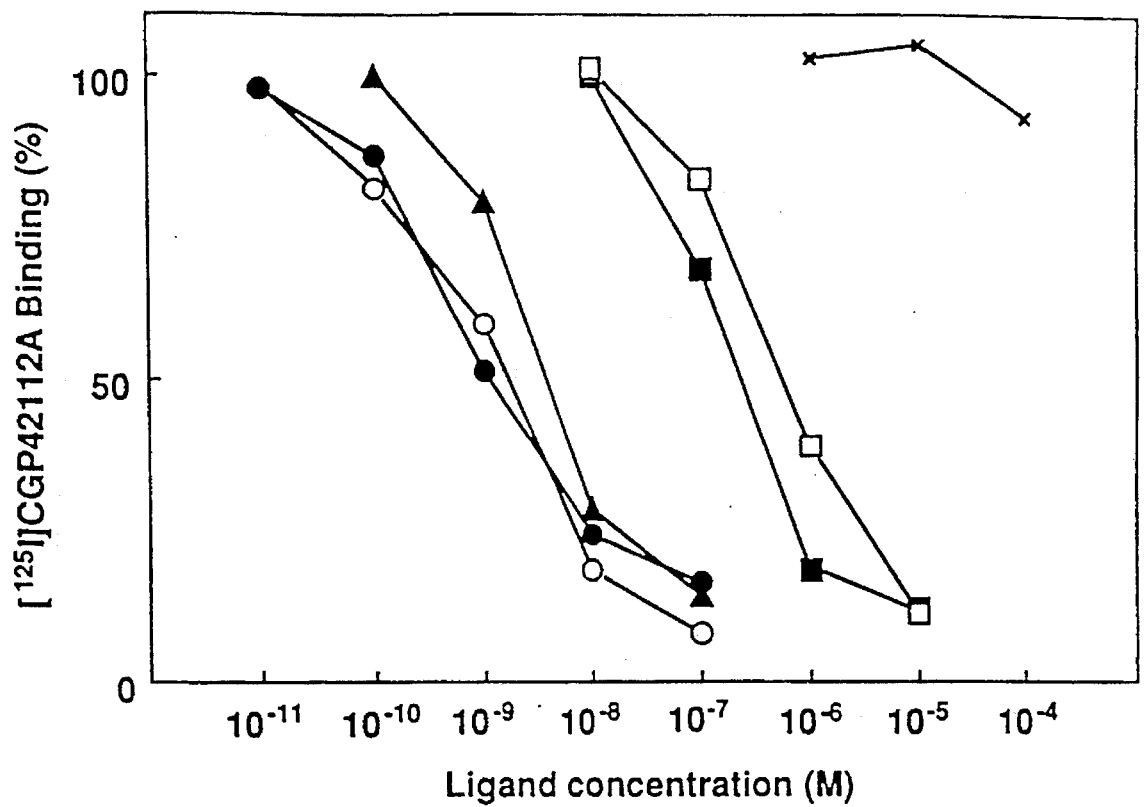

Membranes of COS-7 cells transfected with the cDNA showed specific binding to [$^{125}$I]CGP42112A, a radioligand of the AT$_2$ receptor (Whitebread, S., et al. (1989) Biochem. Biophys. Res. Commun. 163, 284–291). The Scatchard plot of the binding showed K$_d$ and B$_{max}$ of 0.12 nM and 0.57 pmol/mg protein, respectively (FIG. 2A). No specific binding was detectable in untransfected COS-7 cells. Displacement of this binding is shown in FIG. 2B. The binding of [$^{125}$I]CGP42112A was competed by unlabeled angiotensin analogs and AT$_2$ receptor ligands in the following rank order: [Sar$^1$,Ile$^8$]-Ang II=CGP42112A≧Ang II>PD123319>Ang I. DuP753, an AT$_1$-selective antagonist (Chiu, et al. (1989) Biochem. Biophys. Res. Commun. 165, 196–203; Sasaki, K., et al. (1991) Nature 351, 230–233; Murphy, T. J., et al. (1991) Nature 351, 233–236; Sasamura, H., et al. (1992) Biochem. Biophys. Res. Commun. 185, 253–259; Iwai, N., and Inagami, T. (1992) FEBS Lett. 298, 257–260.), was virtually inactive at a concentration up to 10$^{-5}$M. These binding characteristics are in good agreement with those observed in the membranes from whole rat fetus and the cloned rat AT$_2$ receptor.

A comparison of deduced amino acid sequences of the mouse AT$_2$ (SEQ ID NO:02) rat AT$_2$ (SEQ ID NO:3) and mouse AT$_{1a}$ receptors is shown in FIG. 3. The mouse AT$_2$ (SEQ ID NO:04) receptor amino acid sequence is 99% identical to that of the rat AT$_2$ receptor. However, there is only a 34% identity between the mouse AT$_2$ and the mouse AT$_{1a}$ receptor. Hydropathy analysis shows that the mouse AT$_2$ receptor sequence exhibits a conserved transmembrane topology with consensus residues that are found in other seven-transmembrane, G protein-coupled receptors (O'Dowd, B. F., et al. (1989) Annu. Rev. Neurosci. 12, 67–83).

Figure 4B:
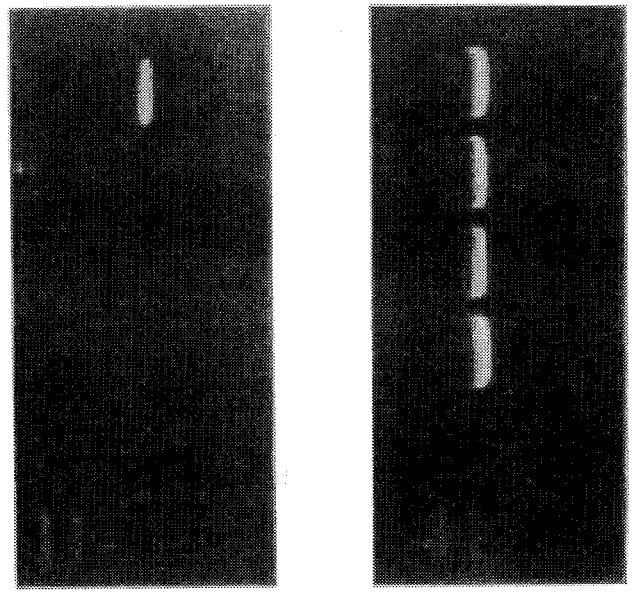
FIGS. 4A and 4B. Northern blot analysis (FIG. 4A) and RT-PCR analysis (FIG. 4B) of mRNA from mouse tissues.
Figure 4A:
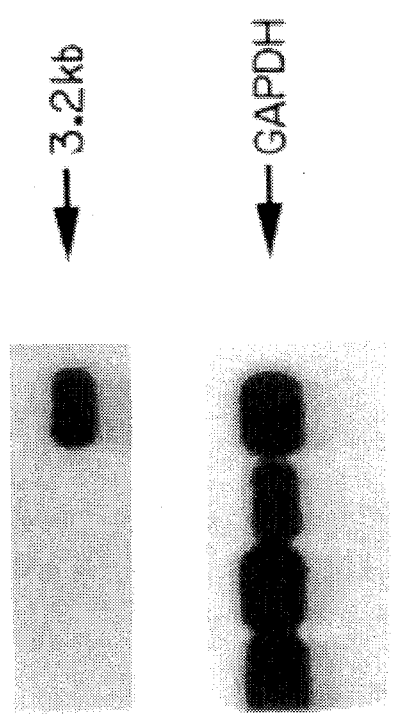

Northern blot analysis shows that the AT$_2$ receptor mRNA is abundant in the whole mouse fetus but undetectable in the heart and liver (FIG. 4A). RT-PCR analysis demonstrates that the AT$_2$ receptor mRNA is expressed abundantly in fetus but at a much lower level in the adult brain (FIG. 4B). This tissue distribution is consistent with the known distribution of the AT$_2$ receptor as reported by ligand binding data of mouse and rat tissues and by Northern blot analysis of rat tissues (Whitebread, S., et al. (1989) supra; Chiu, et al. (1989) supra; Millan, M. A., et al. (1991) Proc. Natl. Acad. Sci. U.S.A. 88, 11440–11444).

Figure 5A:
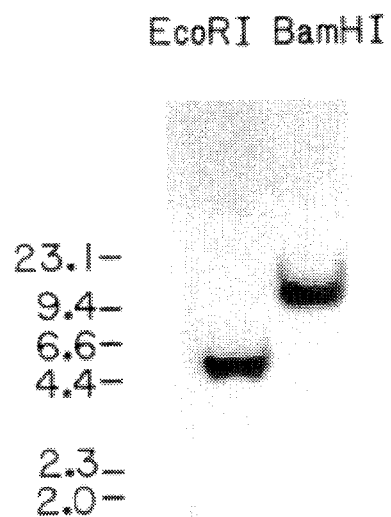
FIG. 5A and 5B. Southern blot hybridization analysis (FIG. 5A) and PCR analysis (FIG. 5B) of the mouse genomic DNA.
Figure 5B:
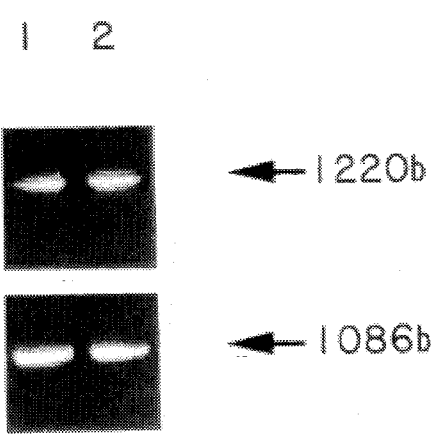

The copy number of the mouse AT$_2$ receptor gene in the mouse genome was determined by Southern blot hybridization analysis (FIG. 5A). The full-length mouse AT$_2$ receptor cDNA was used to probe the mouse genomic DNA digested with two restriction endonucleases, EcoRI and BamHI. Each enzyme generated a single fragment that hybridized to the probe, indicating that the mouse AT$_2$ receptor locus exists as a single copy in the mouse genome. Many G protein-coupled receptors, like b-adrenergic receptor (Kobilka, B. K., et al., (1987) J. Biol. Chem. 264, 7321–7327) and AT$_1$ receptor (Iwai, N., and Inagami, T. (1992) FEBS Lett. 298, 257–260), lack introns in the coding region. However, a number of exceptions are known such as dopamine receptors (Sibley, D. R., and Monsma, F. J. (1992) Trends Pharmacol. Sci. 13, 61–69), tachykinin receptors (Takahashi, K., et al. (1992) Eur. J. Biochem. 204, 1025–1033; Gerard, N. P., et al. (1990) J. Biol. Chem. 265,20455–20462; Hershey, A. D., et al. (1991) J. Biol. Chem. 266, 4366–4374) and endothelin receptors (Hosoda, K., et al. (1992) J. Biol. Chem. 267, 18797–18804; Arai, H., et al.. (1993) J. Biol. Chem. 268, 3463–3470). PCR analysis of the gene for mouse AT$_2$ receptor showed that this gene does not contain introns in the coding region (FIG. 5B).

In the present study, we demonstrate that the structures of mouse and rat AT$_2$ receptors are highly conserved. Mouse AT$_2$ receptor is expressed at high levels during development but is expressed at lower levels in selective tissues in the adult. The mouse AT$_2$ receptor locus exists as a single copy in the mouse genome and the gene for the receptor dose not contain introns in the coding region. In contrast to the AT$_1$ receptor, the actions and the signaling mechanism of the AT$_2$ receptor are not clearly defined. The successful cloning of mouse AT$_2$ receptor cDNA and analysis of its gene described herein enable transgenic studies to further elucidate the functions and the signal mechanisms of the AT$_2$ receptor.

Example 3

Preparation of Stable Transfectants 293 cells, a human embryonic kidney cell line (ATCC), were grown in DMEM supplemented with 10% fetal calf serum. pMRAT2, a rat $AT_2$ receptor full-length cDNA cloned into the expression vector pcDNA I, was cotransfected with the plasmid pSV2neo into 293 cells using the calcium phosphate precipitation method (Southern, P. J. and Berg, P. (1982) J. Mol. Appl. Genet. 1, 327–341). The cells were then subcultured and selected with the antibiotic G418 (800 ug/ml, Gibco-BRL). The antibiotic-resistant cells were cloned by isolation and assayed for the $AT_2$ receptor expression by radioligand binding. The clone expressing the highest number of the $AT_2$ receptor, S293RAT2, was further characterized.

SV-T2 cells, an SV40-transformed Balb/3T3 fibroblast cell line (ATCC), were similarly cotransfected with $pMRAT_2$ and pSV2neo and were selected with 400 ug/ml G418, resulting in the establishment of SV-RAT2, the SV-T2 cell line stably transfected with the rat $AT_2$ receptor cDNA.

Radioligand binding assays with crude membranes from S293RAT2 cells reveal that the cells stably overexpress saturable, single-component, high-affinity binding sites for $[^{125}I]CGP42112A$ characteristic of the $AT_2$ receptor ($K_d$= 0.18 nM, $B_{max}$=10.8 pmol/mg protein). Competition profiles with various angiotensin receptor ligands are essentially identical to those of the $AT_2$ receptor endogenously expressed or transiently overexpressed in COS-7 cells.

It is evident from the above results that one can use the methods and compositions disclosed herein for making and identifying diagnostic probes and therapeutic drugs. It will also be clear to one skilled in the art from a reading of this disclosure that advantage can be taken to effect alterations of angiotensin II responsiveness in a host.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid other than a natural chromosome encoding the amino acid sequence of SEQ ID NO:2 or SEQ ID NO:3.

2. An isolated nucleic acid according to claim 1 having the sequence of SEQ ID NO:1 or SEQ ID NO:5.

3. An isolated nucleic acid consisting of the coding sequence of SEQ ID NO: 1 or (SEQ ID NO:5.

4. A vector comprising a nucleic acid encoding the amino acid sequence of SEQ ID NO:2 or SEQ ID NO:3 operably linked to a transcription regulatory element.

5. A cell comprising a nucleic acid encoding the amino acid sequence of SEQ ID NO:2 or SEQ ID NO:3 operably linked to a transcription regulatory element and flanked by other than its natural sequence.

* * * * *